(12) United States Patent
De et al.

(10) Patent No.: US 7,981,445 B2
(45) Date of Patent: Jul. 19, 2011

(54) COMPOSITIONS AND METHODS FOR PREPARATION OF POORLY WATER SOLUBLE DRUGS WITH INCREASED STABILITY

(75) Inventors: Tapas De, Los Angeles, CA (US); Neil P. Desai, Los Angeles, CA (US); Andrew Yang, Rosemead, CA (US); Zachary Yim, Los Angeles, CA (US); Patrick Soon-Shiong, Los Angeles, CA (US)

(73) Assignee: Abraxis Bioscience, LLC, Los Angeles, CA (US)

( * ) Notice: Subject to any disclaimer, the term of this patent is extended or adjusted under 35 U.S.C. 154(b) by 0 days.

(21) Appl. No.: 12/402,358

(22) Filed: Mar. 11, 2009

(65) Prior Publication Data
US 2009/0196933 A1  Aug. 6, 2009

Related U.S. Application Data

(63) Continuation of application No. 11/513,756, filed on Aug. 30, 2006.

(60) Provisional application No. 60/712,865, filed on Aug. 31, 2005, provisional application No. 60/736,962, filed on Nov. 14, 2005, provisional application No. 60/736,931, filed on Nov. 14, 2005.

(51) Int. Cl.
*A61K 31/7072* (2006.01)
*A61K 31/337* (2006.01)
*A61K 31/282* (2006.01)
*A61K 9/14* (2006.01)
*A61K 33/24* (2006.01)

(52) U.S. Cl. .......... 424/489; 514/449; 514/49; 514/492; 424/649

(58) Field of Classification Search .......... 424/489, 424/649; 514/449, 49, 492
See application file for complete search history.

(56) References Cited

U.S. PATENT DOCUMENTS

| | | | |
|---|---|---|---|
| 4,814,470 A | 3/1989 | Colin et al. |
| 4,826,689 A | 5/1989 | Violanto |
| 4,960,799 A | 10/1990 | Nagy |
| 5,118,528 A | 6/1992 | Fessi et al. |
| 5,145,684 A | 9/1992 | Liversidge et al. |
| 5,334,582 A | 8/1994 | Blackburn et al. |
| 5,362,478 A | 11/1994 | Desai et al. |
| 5,439,686 A | 8/1995 | Desai et al. |
| 5,498,421 A | 3/1996 | Grinstaff et al. |
| 5,637,625 A | 6/1997 | Haynes |
| 5,639,473 A | 6/1997 | Grinstaff et al. |
| 5,650,156 A | 7/1997 | Grinstaff et al. |
| 5,665,382 A | 9/1997 | Grinstaff et al. |
| 5,665,383 A | 9/1997 | Grinstaff et al. |
| 5,681,846 A | 10/1997 | Trissel |
| 5,714,520 A | 2/1998 | Jones et al. |
| 5,725,804 A | 3/1998 | Yen |
| 5,731,355 A | 3/1998 | Jones et al. |
| 5,731,356 A | 3/1998 | Jones et al. |
| 5,731,366 A | 3/1998 | Moench et al. |
| 5,731,556 A | 3/1998 | Gardner et al. |
| 5,733,888 A | 3/1998 | Carver et al. |
| 5,770,222 A | 6/1998 | Unger et al. |
| 5,908,869 A | 6/1999 | Jones et al. |
| 5,916,596 A | 6/1999 | Desai et al. |
| 5,977,164 A | 11/1999 | Carver et al. |
| 5,997,904 A | 12/1999 | Magdassi et al. |
| 6,022,985 A | 2/2000 | Authelin et al. |
| 6,028,108 A | 2/2000 | George |
| 6,071,974 A | 6/2000 | Patel et al. |
| 6,090,844 A | 7/2000 | Han et al. |
| 6,096,331 A | 8/2000 | Desai et al. |
| 6,100,302 A | 8/2000 | Pejaver et al. |
| 6,120,805 A | 9/2000 | Spenlehauer et al. |
| 6,140,373 A | 10/2000 | May et al. |
| 6,140,374 A | 10/2000 | May et al. |
| 6,147,122 A | 11/2000 | Mirejovsky et al. |
| 6,150,423 A | 11/2000 | Carpenter |
| 6,177,477 B1 | 1/2001 | George et al. |
| 6,217,886 B1 | 4/2001 | Önyüksel et al. |
| 6,326,406 B1 | 12/2001 | De Tommaso |
| 6,399,087 B1 | 6/2002 | Zhang et al. |
| 6,469,069 B1 | 10/2002 | Mirejovsky et al. |
| 6,506,405 B1 | 1/2003 | Desai et al. |

(Continued)

FOREIGN PATENT DOCUMENTS

| | | |
|---|---|---|
| EP | 0 835 657 B1 | 8/2004 |
| EP | 1 862 183 A1 | 12/2007 |
| WO | WO-94/12031 A1 | 6/1994 |
| WO | WO-94/12198 A1 | 6/1994 |
| WO | WO-94/18954 A1 | 9/1994 |
| WO | WO-97/33552 A1 | 9/1997 |
| WO | WO-97/49390 A1 | 12/1997 |
| WO | WO-98/14174 A1 | 4/1998 |
| WO | WO-98/14175 A1 | 4/1998 |
| WO | WO-98/23646 A2 | 6/1998 |

(Continued)

OTHER PUBLICATIONS

De, T. et al. (Apr. 2005). "Nab-028, a Nanoparticle Albumin-Bound Novel Taxane, Shows Improved Efficacy and Lower Toxicity over the Tween Formulation (Tween-028)," *Proc. Amer. Assoc. Cancer Res.* 46(Suppl. S): 335, Abstract No. 1432, located at http://aacrmeetingabstracts.org/cgi/content/abstract/2005/1/335-b, last visited Oct. 11, 2010, 2 pages.

(Continued)

*Primary Examiner* — James D Anderson
*Assistant Examiner* — Zohreh Vakili
(74) *Attorney, Agent, or Firm* — Morrison & Foerster LLP

(57) ABSTRACT

The present invention provides stable pharmaceutical compositions of poorly water soluble pharmaceutical agents and stabilizing agents which function to increase stability of the compositions. The use of stabilizing agents provide extended stability of nanoparticle suspensions and other formulations of poorly water soluble pharmaceutical agents such as docetaxel under certain conditions, for example upon dilution for administration.

14 Claims, 7 Drawing Sheets

U.S. PATENT DOCUMENTS

| | | | |
|---|---|---|---|
| 6,528,067 B1 | 3/2003 | Magdassi et al. | |
| 6,534,547 B1 | 3/2003 | Carpenter | |
| 6,537,539 B2 | 3/2003 | Li et al. | |
| 6,537,579 B1 | 3/2003 | Desai et al. | |
| 6,610,317 B2 | 8/2003 | Straub et al. | |
| 6,638,537 B2 | 10/2003 | Dennis et al. | |
| 6,652,884 B2 | 11/2003 | Falciani | |
| 6,726,919 B2 | 4/2004 | Pace et al. | |
| 6,743,436 B1 | 6/2004 | Lee et al. | |
| 6,749,868 B1 | 6/2004 | Desai et al. | |
| 6,753,006 B1 | 6/2004 | Desai et al. | |
| 6,838,569 B2 | 1/2005 | Sharma et al. | |
| 6,914,130 B2* | 7/2005 | Gao et al. | 530/387.9 |
| 6,919,370 B2 | 7/2005 | Chen | |
| 7,041,705 B2 | 5/2006 | Mishra et al. | |
| 7,060,285 B2 | 6/2006 | Muller | |
| 7,060,724 B2 | 6/2006 | Li et al. | |
| 7,175,850 B2 | 2/2007 | Cevc | |
| 7,332,568 B2 | 2/2008 | Trieu et al. | |
| 2002/0039594 A1 | 4/2002 | Unger | |
| 2002/0041897 A1* | 4/2002 | Dang | 424/486 |
| 2002/0159952 A1 | 10/2002 | Unger | |
| 2003/0099674 A1 | 5/2003 | Chen | |
| 2003/0157161 A1 | 8/2003 | Hunter et al. | |
| 2003/0158249 A1 | 8/2003 | Chi et al. | |
| 2003/0185894 A1 | 10/2003 | Zenoni et al. | |
| 2003/0187062 A1 | 10/2003 | Zenoni et al. | |
| 2003/0199425 A1 | 10/2003 | Desai et al. | |
| 2004/0009168 A1 | 1/2004 | Kaisheva et al. | |
| 2004/0097417 A1 | 5/2004 | DeYoung et al. | |
| 2004/0105821 A1* | 6/2004 | Bernstein et al. | 424/46 |
| 2004/0116720 A1 | 6/2004 | Sharma et al. | |
| 2004/0126360 A1 | 7/2004 | Manning et al. | |
| 2004/0143004 A1 | 7/2004 | Fargnoli et al. | |
| 2004/0171560 A1 | 9/2004 | Mukherjee et al. | |
| 2004/0204372 A1 | 10/2004 | Cohen et al. | |
| 2005/0004002 A1 | 1/2005 | Desai et al. | |
| 2005/0019266 A1 | 1/2005 | Unger et al. | |
| 2005/0043272 A1 | 2/2005 | Platt et al. | |
| 2005/0152979 A1 | 7/2005 | Besman et al. | |
| 2005/0238649 A1 | 10/2005 | Doronina et al. | |
| 2006/0079672 A1 | 4/2006 | Glidden | |
| 2006/0121119 A1 | 6/2006 | Zenoni et al. | |
| 2006/0127445 A1 | 6/2006 | Hunter et al. | |
| 2006/0188566 A1* | 8/2006 | Liversidge et al. | 424/451 |
| 2006/0217436 A1 | 9/2006 | Li et al. | |
| 2006/0263434 A1* | 11/2006 | Desai et al. | 424/489 |
| 2007/0020337 A1 | 1/2007 | Zenoni et al. | |
| 2007/0025910 A1 | 2/2007 | Norenberg | |
| 2007/0082838 A1 | 4/2007 | De et al. | |
| 2007/0087022 A1 | 4/2007 | Desai et al. | |
| 2007/0092563 A1 | 4/2007 | Desai et al. | |
| 2007/0093547 A1 | 4/2007 | Desai et al. | |
| 2007/0116774 A1 | 5/2007 | Desai et al. | |
| 2007/0117133 A1 | 5/2007 | Trieu et al. | |
| 2007/0117744 A1 | 5/2007 | Desai et al. | |
| 2007/0129448 A1 | 6/2007 | Desai et al. | |
| 2007/0142457 A1 | 6/2007 | Pontiroli et al. | |
| 2007/0166388 A1 | 7/2007 | Desai et al. | |
| 2007/0196361 A1 | 8/2007 | Soon-Shiong et al. | |
| 2008/0063724 A1 | 3/2008 | Desai et al. | |
| 2008/0128314 A1 | 6/2008 | Takeda et al. | |
| 2008/0146651 A1 | 6/2008 | Jee et al. | |
| 2008/0153738 A1 | 6/2008 | Desai et al. | |
| 2008/0153739 A1 | 6/2008 | Desai et al. | |
| 2008/0161382 A1 | 7/2008 | Desai et al. | |
| 2008/0166839 A1 | 7/2008 | Desai et al. | |
| 2008/0280987 A1 | 11/2008 | Desai et al. | |
| 2009/0048331 A1 | 2/2009 | Soon-Shiong et al. | |
| 2009/0098210 A1 | 4/2009 | Desai et al. | |
| 2009/0263483 A1 | 10/2009 | Desai et al. | |
| 2010/0196490 A1 | 8/2010 | Desai et al. | |

FOREIGN PATENT DOCUMENTS

| | | | |
|---|---|---|---|
| WO | WO-98/23646 A3 | 6/1998 | |
| WO | WO-98/45331 A2 | 10/1998 | |
| WO | WO-98/45331 A3 | 10/1998 | |
| WO | WO-99/00113 C1 | 1/1999 | |
| WO | WO-99/12640 A1 | 3/1999 | |
| WO | WO-99/33780 A1 | 7/1999 | |
| WO | WO-99/39696 A1 | 8/1999 | |
| WO | WO-99/43344 A2 | 9/1999 | |
| WO | WO-00/06152 A1 | 2/2000 | |
| WO | WO-00/23050 A1 | 4/2000 | |
| WO | WO-00/40269 A2 | 7/2000 | |
| WO | WO-00/40269 A3 | 7/2000 | |
| WO | WO-00/44369 A1 | 8/2000 | |
| WO | WO-00/59472 A1 | 10/2000 | |
| WO | WO-00/71079 A2 | 11/2000 | |
| WO | WO-01/15675 A2 | 3/2001 | |
| WO | WO-01/15675 A3 | 3/2001 | |
| WO | WO-01/37808 A1 | 5/2001 | |
| WO | WO-01/72299 A1 | 10/2001 | |
| WO | WO-01/72300 A1 | 10/2001 | |
| WO | WO-01/89522 A1 | 11/2001 | |
| WO | WO-02/079748 A2 | 10/2002 | |
| WO | WO-02/079748 A3 | 10/2002 | |
| WO | WO-02/087545 A1 | 11/2002 | |
| WO | WO-03/017977 A1 | 3/2003 | |
| WO | WO-03/047577 A2 | 6/2003 | |
| WO | WO-03/047577 A3 | 6/2003 | |
| WO | WO-03/053350 A2 | 7/2003 | |
| WO | WO-03/053350 A3 | 7/2003 | |
| WO | WO-03/096944 A1 | 11/2003 | |
| WO | WO-2004/052401 A2 | 6/2004 | |
| WO | WO-2004-052401 A3 | 6/2004 | |
| WO | WO-2004/078747 A1 | 9/2004 | |
| WO | WO-2004/078747 C1 | 9/2004 | |
| WO | WO-2004/094476 A2 | 11/2004 | |
| WO | WO-2004/094476 A3 | 11/2004 | |
| WO | WO-2005/000900 A1 | 1/2005 | |
| WO | WO-2005/051444 A2 | 6/2005 | |
| WO | WO-2005/052116 A2 | 6/2005 | |
| WO | WO-2005/052116 A3 | 6/2005 | |
| WO | WO-2005/115531 A2 | 12/2005 | |
| WO | WO-2005/115531 A3 | 12/2005 | |
| WO | WO-2006/069388 A2 | 6/2006 | |
| WO | WO-2006/069388 A3 | 6/2006 | |
| WO | WO-2006/089290 A1 | 8/2006 | |
| WO | WO-2006/091780 A2 | 8/2006 | |
| WO | WO-2006/091780 A3 | 8/2006 | |
| WO | WO-2006/133510 A1 | 12/2006 | |
| WO | WO-2007/027819 A2 | 3/2007 | |
| WO | WO-2007/027819 A3 | 3/2007 | |
| WO | WO-2007/027941 A2 | 3/2007 | |
| WO | WO-2007/027941 A3 | 3/2007 | |
| WO | WO-2007/044950 A2 | 4/2007 | |
| WO | WO-2007/044950 A3 | 4/2007 | |
| WO | WO-2007/096900 A1 | 8/2007 | |
| WO | WO-2007/109654 A2 | 9/2007 | |
| WO | WO-2007/109654 A3 | 9/2007 | |

OTHER PUBLICATIONS

Desai, N. P. et al. (Apr. 2006). "Enhanced Efficacy and Safety of Nanoparticle Albumin-Bound Nab-Docetaxel Versus Taxotere," *Proc. Amer. Assoc. Cancer Res.* 47: 1277-c, Abstract No. 5438, located at http://aacrmeetingabstracts.org/cgi/content/abstract/2006/1/1277-c, last visited Oct. 11, 2010, 2 pages.

Desai, N. P. et al. (Nov. 2006). "Enhanced Antitumor Activity and Safety of Albumin-Bound Nab-Docetaxel Versus Polysorbate 80-Based Docetaxel," *EJC Supplement* 4(12):49, Abstract No. 152.

Trieu, V. et al. (Apr. 2006). "Improved Effectiveness of Abraxane versus Taxotere in Multiple Different Xenografts," *Proc. Amer. Assoc. Cancer Res.* 47: 1277, Abstract No. 5437, located at http://aacrmeetingabstracts.org/cgi/content/abstract/2006/1/1277-b, last visited Oct. 11, 2010, 2 pages.

U.S. Appl. No. 12/713,092, filed Feb. 25, 2010 for Soon-Shiong et al.
U.S. Appl. No. 12/761,292, filed Apr. 15, 2010, for Desai et al.
U.S. Appl. No. 12/818,099, filed Jun. 17, 2010, for De et al.

U.S. Appl. No. 12/874,965, filed Sep. 2, 2010, for De et al.
U.S. Appl. No. 12/824,014, filed Jun. 25, 2010, for Desai et al.
U.S. Appl. No. 12/832,876, filed Jul. 8, 2010, for Desai et al.
Altmayer, P. et al. (1995). "Propofol Binding to Human Blood Proteins," *Arzneim. Forsc./Drug Res.* 45(II)(10):1053-10556.
Baker, M.T. (Jun. 1, 2001). "Yellowing of Metabisulfate-Containing Propofol Emulsion," *Am. J. Health Syst. Pharm.* 58:1042, 1044, 1046, 1047.
Baker, M.T. et al. (Oct. 2005). "Propofol: The Challenges of Formulation," *Anesthesiology* 103(4):860-876, 17 pages.
Balasubramanian, S.V. et al. (1994). "Taxol-Lipid Interactions: Taxol-Dependent Effects on the Physical Properties of Model Membranes," *Biochemistry* 33:8941-8947.
Balasubramanian, S.V. et al. (Oct. 1994). "Solvent- and Concentration-Dependent Molecular Interactions of Taxol (Paclitaxel)," *J. Pharm. Sci.* 83(10):1470-1476.
Bissery, M.C. et al. (Sep. 15, 1991). "Experimental Antitumor Activity of Taxotere (RP 56976, NSC 628503), a Taxol Analogue," *Cancer Res.* 51(18):4845-4852.
Briggs, L.P. et al. (Nov. 1982). "An Adverse Reaction to the Administration of Disoprofol (Diprivan)," *Anaesthesia* 37(11):1099-1101.
Calabresi, P. et al. (1996). Introduction of "Chemotherapy of Neoplastic Disease," Section X, in *The Pharmacological Basis of Therapeutics*, 9th Edition, McGraw-Hill: New York, NY, pp. 1225-1230.
Carter, D.C. et al. (1994). "Structures of Serum Albumin," in *Advances in Protein Chemistry*, vol. 45: Lipoprotein, Apolipoproteins, and Lipases, Schumaker, V.N., ed., Academic Press, Inc.: San Diego, CA, pp. 153-203.
Cortes, J.E. et al (Oct. 1995). "Docetaxel," *J. Clin. Oncol.* 13(10):2643-2655.
Curry, S. et al. (Sep. 1998). "Crystal Structure of Human Serum Albumin Complexed with Fatty Acid Reveals an Asymmetric Distribution of Binding Sites," *Nat. Struct. Biol.* 5(9):827-835.
Davis, M.A. et al. (1978). "Pulmonary Perfusion Imaging: Acute Toxicity and Safety Factors as a Function of Particle Size," *J. Nucl. Med.* 19(11):1209-1213.
Desai, N.P. et al. (Sep. 2004). "Increased Transport of Nanoparticle Albumin-Bound Paclitaxel (ABI-007) by Endothelial gp6O-Mediated Caveolar Transcytosis: A Pathway Inhibited by Taxol," Poster No. 601, *presented at 16th EORT-NCI-AACR Symposium on Molecular Targets and Cancer Therapeutics*, Geneva, Switzerland, *Eur. J. Cancer* 2(8):182, Abstract.
Dykes, D.J. et al. (1995). "Response of Human Tumor Xenografts in Athymic Nude Mice to Docetaxel, (RP 56976, Taxotere®)," *Invest. New Drugs* 13:1-11.
Fehske, K.J. et al. (1981). "The Location of Drug Binding Sites in Human Serum Albumin," *Biochem. Pharmacol.* 30(7):687-692.
Finlayson, J.S. (1979). "Albumin Products," *Seminars in Thrombosis and Hemostasis* 6(1):85-120.
Flournoy, D.J. (Jul. 1991). "In Vitro Antimicrobial Properties of Deferoxamine Mesylate," *Eur. J. Clin. Microbiol. Infect. Dis.* 10(7):597-598.
Garrido, M.J. et al. (Nov.-Dec. 1994). "Caracterización de la Fijación de Propofol a las Proteínas Plasmáticas y Posibles Interacciones," *Rev. Esp. Anestesiol. Reanim.* 41(6):308-312. [English abstract only, one page.].
Gelderblom, H. et al. (Sep. 2001). "Cremophor EL: The Drawbacks and Advantages of Vehicle Selection for Drug Formulation," *Eur. J. of Cancer* 37(13):1590-1598.
Gupta, S. et al. (Apr. 4, 2003). "Development of a Multidose Formulation for a Humanized Monoclonal Antibody Using Experimental Design Techniques," *AAPS PharmSci.* 5(2):1-9.
Hauser, C.J. et al. (Jun. 1980). "Oxygen Transport Responses to Colloids and Crystalloids in Critically Ill Surgical Patients," *Surg. Gynecol. Obstet.* 150(6):811-816.
He, X.M. et al. (Jul. 16, 1992). "Atomic Structure and Chemistry of Human Serum Albumin," *Nature* 358:209-215.
International Search Report mailed on Feb. 28, 2007, for International Application No. PCT/US2006/033931, filed on Aug. 30, 2006, four pages.

Joint FAO/WHO Expert Committee on Food Additives. (1971). "A Review of the Technological Efficacy of Some Antimicrobial Agents," *FAO Nutritional Meetings Reports Series No. 48C WHO/FOOD Add./70/4*, pp. 1-61.
Keowmaneechai, E. et al. (Nov. 20, 2002). "Influence of EDTA and Citrate on Physicochemical Properties of Whey Protein-Stabilized Oil-in-Water Emulsions Containing $CaCl_2$," *J. Agric. Food Chem.* 50(24):7145-7153.
Kragh-Hansen, U. (Feb. 1990). "Structure and Ligand Binding Properties of Human Serum Albumin," *Dan. Med. Bull.* 37(1):57-84.
Lam, X.M. et al. (Jun. 1997). "The Effect of Benzyl Alcohol on Recombinant Human Interferon-Gamma," *Pharm. Res.* 14(6):725-729.
Mollison, P. L. (Jan. 2000). "The Introduction of Citrate as an Anticoagulant for Transfusion and of Glucose as a Red Cell Preservative," *Br. J. Haematol.* 108(1):13-18.
Paál, K. et al. (Apr. 2001). "High Affinity Binding of Paclitaxel to Human Serum Albumin," *Eur. J. Biochem.* 268(7):2187-2191.
Purcell, M. et al. (Mar. 16, 2000). "Interaction of Taxol with Human Serum Albumin," *Biochim. Biophys. Acta* 1478(1):61-68.
Schroeder, H.G. et al. (Apr. 1978). "Distribution of Radiolabeled Subvisible Microspheres after Intravenous Administration to Beagle Dogs," *J. Pharm Sci.* 67(4):504-507.
Schroeder, H.G. et al. (Apr. 1978). "Physiological Effects of Subvisible Microspheres Administered Intravenously to Beagle Dogs," *J. Pharm. Sci.* 67(4):508-513.
Sharma, A. et al. (Dec. 15, 1993). "Antitumor Effect of Taxol-Containing Liposomes in a Taxol-Resistant Murine Tumor Model," *Cancer Res.* 53(24):5877-5881.
Sharma, A. et al. (Jun. 1994). "Novel Taxol Formulations: Preparation and Characterization of Taxol-Containing Liposomes," *Pharm. Res.* 11(6):889-896.
Sharma, A. et al. (Dec. 1995). "Antitumor Efficacy of Taxane Liposomes on a Human Ovarian Tumor Xenograft in Nude Athymic Mice," *J. Pharm. Sci.* 84(12):1400-1404.
Sharma, A. et al. (Oct. 22, 1996). "Paclitaxel-Liposomes for Intracavitary Therapy of Intraperitoneal P388 Leukemia," *Cancer Lett.* 107(2):265-272.
Sharma, U.S. et al. (Oct. 1995). "Pharmaceutical and Physical Properties of Paclitaxel (Taxol) Complexes with Cyclodextrins," *J. Pharm. Sci.* 84(10):1223-1230.
Shimoni, E. et al. (Jun. 1994). "Antioxidant Properties of Deferoxamine," *Journal of the American Oil Chemists' Society* 71(6):641-644.
Straubinger, R.M. et al. (1994). "Novel Taxol Formulations: Taxol-Containing Liposomes," *J. Natl. Cancer Inst. Monogr.* (15):69-78.
Sugio, S. et al. (1999). "Crystal Structure of Human Serum Albumin at 2.5 Å Resolution," *Protein. Eng.* 12(6):439-446.
Sutton, S.V.W. et al. (Nov.-Dec. 2002). "Development of the Antimicrobial Effectiveness Test as USP Chapter <51>," *PDA J. Pharm. Sci. Tech.* 56(6):300-311.
Tomiak, E. et al. (Jul. 1994). "Phase I Study of Docetaxel Administered as a 1-Hour Intravenous Infusion on a Weekly Basis," *J. Clin. Oncol.* 12(7):1458-1467.
Tullis, J.L. (Jan. 31, 1977). "Albumin: 2. Guidelines for Clinical Use," *The Journal of the American Medical Association* 237(5):460-463.
Urien, S. et al. (May 1996). "Docetaxel Serum Protein Binding with High Affinity of $Alpha_1$-Acid Glycoprotein," *Invest. New Drugs* 14(2):147-151.
Villiere, A. et al. (2005; e-pub. Feb. 12, 2005). "Oxidative Stability of Bovine Serum Albumin- and Sodium Caseinate-Stabilized Emulsions Depends on Metal Availability," *J. Agric. Food Chem.* 53(5):1514-1520.
Wolin, M.J. (May 1966). "Lysis of *Vibrio succinogenes* by Ethylenediamine-tetraacetic Acid or Lysozyme," *J. Bacteriol.* 91(5):1781-1786.
Vorum, H. (Nov. 1999). "Reversible Ligand Binding to Human Serum Albumin," *Dan. Med. Bull.* 46(5):379-399.
Waugh, W.N. et al. (Jul. 1991). "Stability, Compatibility, and Plasticizer Extraction of Taxol (NSC-125973) Injection Diluted in Infusion Solutions and Stored in Various Containers," *Am. J. Hosp. Pharmacists* 48(7):1520-1524.

Wooley, R.E. et al. (Jun. 1983). "Action of EDTA-Tris and Antimicrobial Agent Combinations on Selected Pathogenic Bacteria," *Vet. Microbiol.* 8(3):271-280.

Yokel, R.A. et al. (1981). "Acute Toxicity of Latex Microspheres," *Toxicol. Lett.* 9:165-170.

U.S. Appl. No. 09/446,783, filed May 16, 2000 for Desai et al.
U.S. Appl. No. 09/937,840, filed Jan. 28, 2002 for Desai et al.
U.S. Appl. No. 11/553,339, filed Oct. 26, 2006 for Desai et al.
U.S. Appl. No. 12/051,782, filed Mar. 19, 2008 for Desai et al.
U.S. Appl. No. 12/240,893, filed Sep. 29, 2008 for Desai et al.
U.S. Appl. No. 12/271,748, filed Nov. 14, 2008, for Desai et al.
U.S. Appl. No. 60/655,934, filed Feb. 24, 2005, for Liversidge et al.
U.S. Appl. No. 12/331,924, filed Dec. 10, 2008, for Desai et al.
U.S. Appl. No. 12/334,115, filed Dec. 12, 2008, for Desai et al.
U.S. Appl. No. 12/422,011, filed Apr. 10, 2009, for Desai et al.
U.S. Appl. No. 12/436,697, filed May 6, 2009, for Desai et al.
U.S. Appl. No. 12/474,218, filed May 28, 2009, for Desai et al.
U.S. Appl. No. 12/479,710, filed Jun. 5, 2009, for Desai et al.
U.S. Appl. No. 12/513,843, filed May 6, 2009, for Desai et al.
U.S. Appl. No. 12/519,126 internationally filed on Jun. 12, 2006, for Desai et al.
U.S. Appl. No. 12/530,188 internationally filed on Mar. 7, 2008 for Desai et al.
U.S. Appl. No. 12/598,406 internationally filed on May 5, 2008 for Desai et al.
U.S. Appl. No. 12/600,991, filed Nov. 19, 2009 for Desai et al.
U.S. Appl. No. 12/910,693, filed Oct. 22, 2010 for Desai et al.
U.S. Appl. No. 13/038,287, filed on Mar. 1, 2011, for Desai et al.

* cited by examiner 7A 7B

COMPOSITIONS AND METHODS FOR PREPARATION OF POORLY WATER SOLUBLE DRUGS WITH INCREASED STABILITY

CROSS-REFERENCE TO RELATED APPLICATIONS

This application is a continuation of U.S. application Ser. No. 11/513,756, filed Aug. 30, 2006, which claims the priority benefit of U.S. Provisional Application 60/712,865 filed Aug. 31, 2005, U.S. Provisional Application 60/736,962 filed Nov. 14, 2005, and U.S. Provisional Application 60/736,931 filed Nov. 14, 2005, all of which are hereby incorporated herein by reference in their entireties.

BACKGROUND OF THE INVENTION

There is an ever increasing number of pharmaceutical drugs being formulated that are poorly soluble or insoluble in aqueous solutions. Such drugs provide challenges to delivering them in an injectable form such as through parenteral administration. A well-designed formulation must, at a minimum, be capable of presenting a therapeutically effective amount of the poorly soluble drug to the desired absorption site, in an absorbable form. In addition, these compositions tend to be unstable, with sedimentation and/or precipitation occurring in under 24 hours following rehydration or reconstitution.

Taxanes, in particular the two currently available taxane drugs, paclitaxel and docetaxel, are potent antitumor agents. Paclitaxel is very poorly water soluble (less than 10 μg/mL), and as a result, cannot be practically formulated with an aqueous medium for IV administration. Currently, paclitaxel is formulated for IV administration to patients with cancer in a solution with polyoxyethylated castor oil (Polyoxyl 35 or Cremophor®) as the primary solvent/surfactant, with high concentrations of ethanol employed as co-solvent. One of the major difficulties in the administration of paclitaxel is the occurrence of hypersensitivity reactions. These reactions, which include severe skin rashes, hives, flushing, dyspnea, tachycardia and others, may be attributed at least in part to the high concentrations of ethanol and Cremophor used as solvents in the formulation. Docetaxel, an analog of paclitaxel, is semisynthetically produced from 10-deacetyl baccatin III, a noncytotoxic precursor extracted from the needles of *Taxus baccata* and esterified with a chemically synthesized side chain (Cortes and Pazdur, 1995, *J. Clin. Oncol.* 13(10):2643-55). Like paclitaxel, docetaxel is very poorly soluble in water. Currently, the most preferred solvent/surfactant used to dissolve docetaxel is polysorbate 80 (Tween 80) (Bissery et al. 1991 *Cancer Res.* 51(18):4845-52; Tomiak et al. 1992). Like Cremophor, Tween often causes hypersensitivity reactions in patients. Further, Tween 80 cannot be used with PVC delivery apparatus because of its tendency to leach diethylhexyl phthalate, which is highly toxic.

Purification of semi-synthetic paclitaxel and docetaxel is a challenging problem due to the formation of a number of degradation products along the synthetic route. Furthermore, purified taxanes are found to undergo degradation, even under controlled storage conditions. Therefore, it becomes desirable to develop stable forms of these molecules which retain the desirable anti-cancer properties. Previous efforts in obtaining suitable docetaxel have been focusing on processes of preparing trihydrate forms of docetaxel, which were believed to have substantially greater stability than that of the anhydrous product. See, e.g., U.S. Pat. Nos. 6,022,985; 6,838,569.

In order to attain the expected therapeutic effects of poorly water soluble agents such as paclitaxel and docetaxel, it is usually required that a solubilized form or nanodispersed form of the agent be administered to a patient.

Thus, a number of methods have been developed which are based on the use of: auxiliary solvents; surfactants; soluble forms of the drug, e.g., salts and solvates; chemically modified forms of the drug, e.g., prodrugs; soluble polymer-drug complexes; special drug carriers such as liposomes; and others. Indeed, the use of amphiphilic block copolymer micelles has attracted a great deal of interest as a potentially effective drug carrier which is capable of solubilizing a hydrophobic drug in an aqueous environment.

Each of the above methods is hampered by one or more particular problems. For example, the method based on the use of surfactant micelles to solubilize hydrophobic drugs has problems in that some of the surfactants are relatively toxic and precipitation of hydrophobic drugs occurs when subjected to dilution.

Previously, phospholipid-based liposome formulations for paclitaxel, Taxotere, and other active taxanes have been developed (Straubinger et al. 1993, *J. Natl. Cancer Inst. Monogr.* (15):69-78; Straubinger et al. 1994; Sharma et al. 1993, *Cancer Res.* 53(24):557-81; Sharma and Straubinger 1994, *Pharm. Res.* 11(6):889-96; A. Sharma et al. 1995, *J. Pharm. Sci.* 84(12): 1400-4), and the physical properties of these and other taxane formulations have been studied (Sharma and Straubinger 1994, *Pharm. Res.* 11(6):889-96; U. S. Sharma et al. 1995, *J. Pharm. Sci.* 84(10):1223-30; Balasubramanian and Straubinger 1994, *Biochemistry* 33(30):8941-7; Balasubramanian et al. 1994, *J. Pharm. Sci.* 83(10):1470-6). The main utility of these formulations is the elimination of toxicity related to the Cremophor EL excipient, and a reduction in the toxicity of the taxane itself, as demonstrated in several animal tumor models (Sharma et al. 1993, *Cancer Res.* 53(24):557-81; A. Sharma et al. 1995, *J. Pharm. Sci.* 84(12):1400-4; Sharma et al. 1996, *Cancer Lett.* 107(2):265-272). This observation holds for several taxanes in addition to paclitaxel (A. Sharma et al. 1995, *J. Pharm. Sci.* 84(12):1400-4). In some cases, the antitumor potency of the drug appears to be slightly greater for the liposome-based formulations (Sharma et al. 1993, *Cancer Res.* 53(24):557-81).

These liposomal formulations comprise phospholipids and other additives, in addition to the taxane, and may be stored in a dried state. Upon addition of an aqueous phase to the mixture, particles form spontaneously and may take the form of liposomes (Straubinger et al. 1993). Liposomes are closed, vesicular structures consisting of a limiting bilayer membrane surrounding an aqueous core. A preferred formulation composition (Sharma and Straubinger 1994) contains a neutral (zwitterionic) phospholipid such as lecithin (phosphatidylcholine, 80-90% by mole ratio), along with a negatively charged phospholipid such as phosphatidylglycerol (10-20%). The latter prevents aggregation of the particles through electrostatic repulsion. The most stable taxane content is in the range of 3-4 mole % (relative to total phospholipid content); such liposomes may be physically and/or chemically stable for 2 months after hydration. Under most conditions, paclitaxel formulations containing higher (e.g. 8 mole %) drug concentrations are very unstable and may precipitate within minutes of preparation (Sharma and Straubinger 1994).

The greatest concern over these formulations has been the relatively low taxane content of acceptably stable formulations (3-5 mole %), which necessitates the administration of a large amount of phospholipid (5-10 gm) to patients in order to give the anticipated dose of drug. Although humans frequently are given large amounts of lipids intravenously for Total Parenteral Nutrition (TPN), a major developmental aim has been to produce taxane liposomes having a higher taxane content.

Other approaches to formulating poorly soluble drug for oral or parenteral delivery include, for example, formulations in which the poorly soluble drug is an oil-in-water emulsion, a microemulsion, or a solution of micelles or other multilamellar carrier particles. While such approaches may be appropriate for some ionizable as well as non-ionizable hydrophobic therapeutic agents, they fail to take advantage of the unique acid-base chemical properties, and associated solubility properties, of ionizable compounds.

Drugs that are insoluble in water can have significant benefits when formulated as a stable suspension of sub-micron particles. Accurate control of particle size is essential for safe and efficacious use of these formulations. Particles must be less than seven microns in diameter to safely pass through capillaries without causing emboli (Allen et al., 1987; Davis and Taube, 1978; Schroeder et al., 1978; Yokel et al., 1981, *Toxicol. Lett.* 9(2): 165-70).

Another approach is disclosed in U.S. Pat. No. 5,118,528 which discloses a process for preparing nanoparticles. The process includes the steps of: (1) preparing a liquid phase of a substance in a solvent or a mixture of solvents to which may be added one or more surfactants, (2) preparing a second liquid phase of a non-solvent or a mixture of non-solvents, the non-solvent being miscible with the solvent or mixture of solvents for the substance, (3) adding together the solutions of (1) and (2) with stirring and (4) removing of unwanted solvents to produce a colloidal suspension of nanoparticles. The '528 patent discloses that it produces particles of the substance smaller than 500 nm without the supply of energy. In particular the '528 patent states that it is undesirable to use high energy equipment such as sonicators and homogenizers.

U.S. Pat. No. 4,826,689 discloses a method for making uniformly sized particles from water-insoluble drugs or other organic compounds. First, a suitable solid organic compound is dissolved in an organic solvent, and the solution can be diluted with a non-solvent. Then, an aqueous precipitating liquid is infused, precipitating non-aggregated particles with substantially uniform mean diameter. The particles are then separated from the organic solvent. Depending on the organic compound and the desired particle size, the parameters of temperature, ratio of non-solvent to organic solvent, infusion rate, stir rate, and volume can be varied according to the patent. The '689 patent discloses that this process forms a drug in a metastable state which is thermodynamically unstable and which eventually converts to a more stable crystalline state. The '689 patent discloses trapping the drug in a metastable state in which the free energy lies between that of the starting drug solution and the stable crystalline form. The '689 patent discloses utilizing crystallization inhibitors (e.g., polyvinylpyrrolidinone) and surface-active agents (e.g., poly(oxyethylene-co-oxypropylene)) to render the precipitate stable enough to be isolated by centrifugation, membrane filtration or reverse osmosis.

Another approach to providing insoluble drugs for parenteral delivery is disclosed in U.S. Pat. No. 5,145,684. The '684 patent discloses the wet milling of an insoluble drug in the presence of a surface modifier to provide a drug particle having an average effective particle size of less than 400 nm. The '684 patent discloses the surface modifier is adsorbed on the surface of the drug particle in an amount sufficient to prevent agglomeration into larger particles. Nanoparticles of insoluble drugs prepared under conditions of high shear forces (e.g., sonication, high pressure homogenization, or the like) with biocompatible polymers (e.g., albumin) are disclosed in, for example, U.S. Pat. Nos. 5,916,596, 6,506,405, and 6,537,579 and also in U.S. Patent Publication 2005/0004002 A1.

In view of the foregoing, there is a need for pharmaceutical compositions comprising poorly water soluble drugs with increased physical and chemical stability, which eliminate the use of physiologically harmful solvents and excipients, and methods of production thereof. It is desirable that such pharmaceutical compositions should not degrade, should remain stable under storage conditions and remain physically and/or chemically stable after rehydration. It would also be desirable to have a pharmaceutical composition comprising an anhydrous form of poorly water soluble drug that has greater solubility in traditionally used solvents and excipients, as well as in solvents and excipients that are not physiologically harmful. The present invention provides such pharmaceutical compositions and methods.

The disclosures of all publications, patents, patent applications and published patent applications referred to herein are hereby incorporated herein by reference in their entireties.

BRIEF SUMMARY OF THE INVENTION

The invention provides compositions and methods of producing stable pharmaceutical formulations of docetaxel. In one embodiment, the invention provides pharmaceutical formulations of docetaxel comprising citrate or derivatives thereof. In a second embodiment, the invention provides pharmaceutical formulations of docetaxel comprising sodium pyrophosphate. In a third embodiment, the invention provides pharmaceutical formulations of docetaxel comprising EDTA or derivative thereof. In a fourth embodiment, the invention provides pharmaceutical formulations of docetaxel comprising sodium gluconate. In a fifth embodiment, the invention provides pharmaceutical formulations of docetaxel comprising citrate and sodium chloride. In a sixth embodiment, the invention provides a formulation of docetaxel comprising a surfactant, wherein the docetaxel used for preparing the formulation is in an anhydrous form prior to being incorporated into the formulation.

Accordingly, in one aspect, the invention provides compositions (such as pharmaceutical compositions) comprising a poorly water soluble pharmaceutical agent (such as docetaxel) and a stabilizing agent, wherein stability of the composition is enhanced as compared to that of a composition without the stabilizing agent. In some embodiments, the compositions further comprise a biocompatible polymer (such as carrier proteins described herein). The stabilizing agent includes, for example, chelating agents (such as citrate, malic acid, edetate, and pentetate), sodium pyrophosphate, and sodium gluconate.

In another aspect, there are provided various compositions (such as pharmaceutical compositions), comprising docetaxel, wherein the docetaxel used for preparation of the composition is in anhydrous form (for example, the docetaxel may be anhydrous prior to being incorporated into the composition). In some embodiments the composition further comprises a biocompatible polymer (such as a carrier protein described herein). In some embodiments, the composition further comprises a stabilizing agent (such as stabilizing agents described herein). In some embodiments, the composition comprises both a biocompatible polymer (such as carrier proteins described herein) and a stabilizing agent. In some embodiments, the invention provides compositions (such as pharmaceutical compositions) comprising docetaxel and a surfactant, wherein the docetaxel used for preparation of the composition is in anhydrous form (for example, the docetaxel may be anhydrous prior to being incorporated into the composition). In some embodiments, the composition further comprises a stabilizing agent (such as stabilizing agents described herein).

Also provided are unit dosage forms of compositions described herein, articles of manufacture comprising the inventive compositions or unit dosage forms in suitable packaging, and kits comprising the compositions. The invention also provides methods of making and using these compositions as described herein.

It is to be understood that one, some, or all of the properties of the various embodiments described herein may be combined to form other embodiments of the present invention.

BRIEF DESCRIPTION OF THE FIGURES

FIGS. 3A-3C show plasma concentration of Nab-docetaxel and Taxotere® at 10 mg/kg, 20 mg/kg, and 30 mg/kg doses, respectively. FIG. 3D shows the linear relationship between AUC (Area Under Curve) and dose for Nab-docetaxel and nonlinear relationship between AUC and dose for Taxotere. Nab-docetaxel exhibited a linear relationship fitted by the equation AUC=218*Dose; Taxotere exhibited an exponential curve fitted by the equation AUC=722*exp(0.10*Dose).

DETAILED DESCRIPTION OF THE INVENTION

Figure 1:
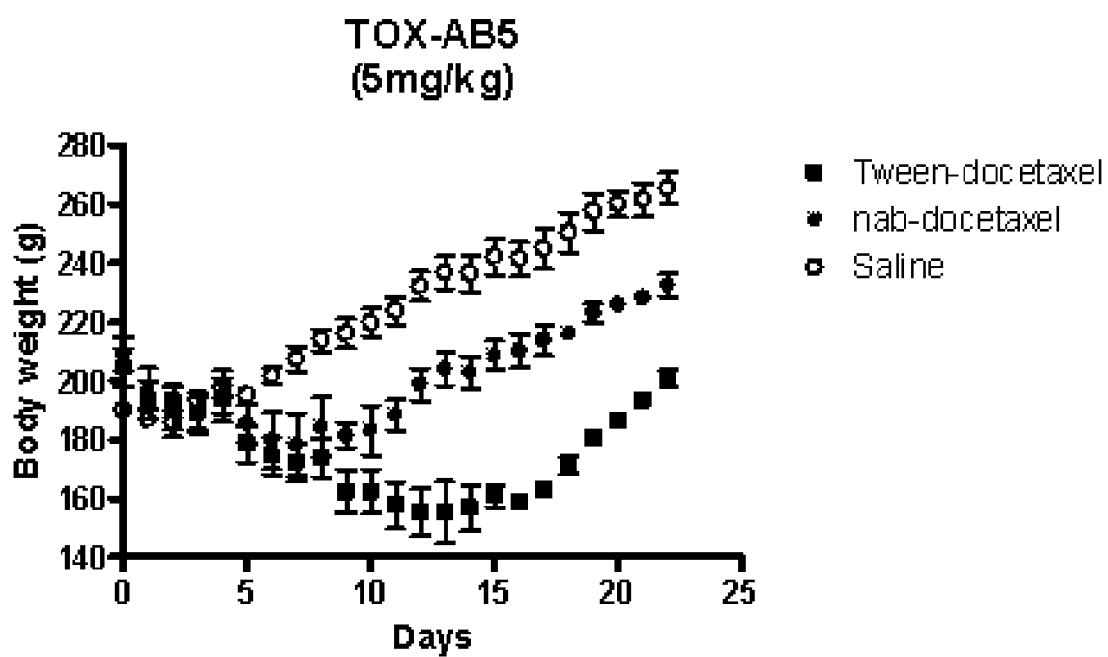
FIG. 1 shows body weight loss of rats at 5 mg/kg docetaxel dose for a nanoparticle albumin formulation of docetaxel (Nab-docetaxel) and Tween 80-docetaxel (Taxotere®). Dosing occurred on days 0, 4, and 8.

The present invention in one of its embodiments provides for compositions and methods of preparation of docetaxel and other poorly water soluble pharmaceutical agents or drugs which retain the desirable therapeutic effects and remain physically and/or chemically stable upon exposure to certain conditions such as prolonged storage, elevated temperature, or dilution for parenteral administration.

A stable composition is, for example, one that remains physically and/or chemically stable and therefore does not show evidence of precipitation or sedimentation for at least about 8 hours, including for example at least about any of 24 hours, 48 hours, or up to about 96 hours following reconstitution or rehydration. For example, the compositions may remain stable for at least 24 hours following reconstitution or rehydration.

Stability of a suspension is generally (but not necessarily) evaluated at usual conditions of transport and storage expected during product distribution (such as room temperature (such as 20-25° C.) or refrigerated conditions (such as 4° C.)). For example, a suspension is stable at a storage temperature if it exhibits no flocculation or particle agglomeration visible to the naked eye or when viewed under the optical microscope at 1000 times (or other suitable particle characterization techniques), at about fifteen minutes after preparation of the suspension. Stability may also be evaluated under exaggerated conditions of temperature, humidity, light, and/or others, to test the stability of the compositions in an accelerated testing. For example, stability can be evaluated at a temperature that is higher than about 40° C. Stability of the composition can also be evaluated, for example, by the ability of the composition to remain suspended without showing evidence of settling or creaming, or by the ability of the composition to remain unchanged (i.e., no visible difference) in terms of color or consistency.

Stability of a dry (such as a lyophilized) composition can be evaluated based on the behavior of the liquid suspension resulting from reconstitution or rehydration of the dry composition.

It is an object of the invention to provide pharmaceutical compositions capable of maintaining physically and/or chemically stabilized, therapeutically effective amounts of poorly water soluble pharmaceutical agents. It is another object of the invention to provide pharmaceutical compositions capable of maintaining a physically and/or chemically stabilized poorly water soluble pharmaceutical agents upon dilution for administration to a patient. It is a further object of the invention to provide pharmaceutical compositions capable of maintaining physically and/or chemically stabilized, therapeutically effective amounts of poorly water soluble pharmaceutical agents with reduced toxicities. It is a further object of the invention to provide stable pharmaceutical formulations using anhydrous docetaxel, as well compositions resulting from use of anhydrous docetaxel.

It is a further object of the invention to provide improved methods of preparing pharmaceutical compositions capable of maintaining physically and/or chemically stabilized, therapeutically effective amounts of poorly water soluble pharmaceutical agents. It is a further object of the invention to provide improved methods of preparing pharmaceutical compositions capable of maintaining a physically and/or chemically stabilized poorly water soluble pharmaceutical agent upon dilution for administration to a patient. It is a further object of the invention to provide improved methods of preparing pharmaceutical compositions capable of maintaining physically and/or chemically stabilized, therapeutically effective amounts of poorly water soluble pharmaceutical agents with reduced toxicities.

In one embodiment the invention provides a sterile pharmaceutical composition for parenteral administration comprised of a poorly water soluble pharmaceutical agent, which is physically and/or chemically stabilized by the addition of excipients to the composition. Prior to the present invention, the relative stability of certain poorly soluble pharmaceutical agents has limited their use in parenteral pharmaceutical compositions due to degradation under storage conditions and/or precipitation upon dilution. Many different pharmaceutical agents could not be satisfactorily prepared as parenterals due to the absence of a stable composition.

The present invention involves the surprising discovery that common excipients such as citrate are capable of stabilizing poorly water soluble pharmaceutical agents such as docetaxel. It is therefore a primary object of the invention to provide compositions comprising docetaxel (and other poorly water soluble pharmaceutical agents) and excipients to obtain stable, parenteral pharmaceutical compositions. Therefore, in one embodiment, the invention provides a pharmaceutical composition comprising docetaxel and citrate. In another embodiment, the invention provides a pharmaceutical composition comprising docetaxel, citrate and sodium chloride.

Various Embodiments of the Invention

The invention provides compositions (such as pharmaceutical compositions) comprising a poorly water soluble pharmaceutical agent and a stabilizing agent, wherein stability of the composition is enhanced as compared to that of a composition without the stabilizing agent. For example, the composition may comprise docetaxel and a stabilizing agent, wherein stability of the composition is enhanced as compared to that of a composition without the stabilizing agent. In some embodiments, the compositions further comprise a biocompatible polymer. In some embodiments, the biocompatible polymer is a carrier protein (such as an albumin, for example, human serum albumin (HSA)). In some embodiments, the stability of the composition is at least 1.5 times (including for example at least about any of 2×, 3×, 4×, 5×, 6×, 7×, 8×, 9×, 10×, 15×, 20×, 25×, 30×, or more) greater as compared to that of a composition without the stabilizing agent. In some embodiments, the poorly water soluble pharmaceutical agent is unstable in a composition not comprising the stabilizing agent.

In some embodiments, there is provided a composition comprising a poorly water soluble pharmaceutical agent and a stabilizing agent, wherein the stabilizing agent is a chelating agent, and wherein stability of the composition is enhanced as compared to that of a composition without the stabilizing agent. In some embodiments, there is provided a composition comprising docetaxel and a stabilizing agent, wherein the stabilizing agent is a chelating agent, and wherein stability of the composition is enhanced as compared to that of a composition without the stabilizing agent. In some embodiments, the composition further comprises a biocompatible polymer. In some embodiments, the biocompatible polymer is a carrier protein (such as albumin, for example, HSA). In some embodiments, the stabilizing agent is a polydentate chelating agent. In some embodiments, the stabilizing agent comprises one or more carboxylic acid groups. In some embodiments, the chelating agent is not deferoxamine (i.e., is other than deferoxamine). In some embodiments, the chelating agent is any of (and in some embodiments selected from the group consisting of) edetate, citrate, malic acid, pentetate, tromethamine, derivatives thereof, and mixtures thereof. In some embodiments, the stabilizing agent is a citrate or a derivative thereof (such as sodium citrate and in some embodiments citric acid). In some embodiments, the composition comprises sodium citrate and sodium chloride. In some embodiments, the composition comprises about 200 mM citrate and about 300 mM sodium chloride. In some embodiments, the stabilizing agent is an edetate or a derivative thereof (such as EDTA).

In some embodiments, there is provided a composition comprising a poorly water soluble pharmaceutical agent and a stabilizing agent, wherein the stabilizing agent is sodium gluconate, and wherein stability of the composition is enhanced as compared to that of a composition without the stabilizing agent. In some embodiments, there is provided a composition comprising docetaxel and a stabilizing agent, wherein the stabilizing agent is sodium gluconate, and wherein stability of the composition is enhanced as compared to that of a composition without the stabilizing agent. In some embodiments, the composition further comprises a biocompatible polymer. In some embodiments, the biocompatible polymer is a carrier protein (such as albumin, for example, HSA).

In some embodiments, there is provided a composition comprising a poorly water soluble pharmaceutical agent and a stabilizing agent, wherein the stabilizing agent is sodium pyrophosphate, and wherein stability of the composition is enhanced as compared to that of a composition without the stabilizing agent. In some embodiments, there is provided a composition comprising docetaxel and a stabilizing agent, wherein the stabilizing agent is sodium pyrophosphate, and wherein stability of the composition is enhanced as compared to that of a composition without the stabilizing agent. In some embodiments, the composition further comprises a biocompatible polymer. In some embodiments, the biocompatible polymer is a carrier protein (such as albumin, for example, HSA).

In some embodiments, the composition comprises a poorly water soluble pharmaceutical agent, an albumin, and a stabilizing agent, wherein the weight ratio of the albumin to the poorly water soluble pharmaceutical agent in the composition is about 0.01:1 to about 100:1, and wherein stability of the composition is enhanced as compared to that of a composition without the stabilizing agent. In some embodiments, the composition comprises a poorly water soluble pharmaceutical agent, an albumin, and a stabilizing agent, wherein the weight ratio of the albumin to the poorly water soluble pharmaceutical agent in the composition is about 18:1 or less (including for example any of about 1:1 to about 18:1, about 2:1 to about 15:1, about 3:1 to about 12:1, about 4:1 to about 10:1, and about 9:1), and wherein stability of the composition is enhanced as compared to that of a composition without the stabilizing agent. In some embodiments, the composition comprises docetaxel, an albumin, and a stabilizing agent, wherein the weight ratio of the albumin to the docetaxel in the composition is about 18:1 or less (including for example any of about 1:1 to about 18:1, about 2:1 to about 15:1, about 3:1 to about 12:1, about 4:1 to about 10:1, and about 9:1), and wherein stability of the composition is enhanced as compared to that of a composition without the stabilizing agent. In some embodiments, the stabilizing agent is a chelating agent, such as any of (and in some embodiments selected from the group consisting of) edetate, citrate, malic acid, pentetate, tromethamine, derivatives thereof, and mixtures thereof. In some embodiments, the stabilizing agent is a citrate or a derivative thereof (such as sodium citrate). In some embodiments, the composition comprises sodium citrate and sodium chloride. In some embodiments, the stabilizing agent is an edetate or a derivative thereof (such as EDTA). In some embodiments, the stabilizing agent is sodium gluconate. In some embodiments, the stabilizing agent is sodium pyrophosphate.

In some embodiments, the protein/pharmaceutical agent is in particulate form(s), which in various embodiments may be of average diameters as described herein.

In some embodiments, the composition comprises a protein-associated poorly water soluble pharmaceutical agent and a stabilizing agent, wherein stability of the composition is enhanced as compared to that of a composition without the stabilizing agent. In some embodiments, the composition comprises a protein-associated docetaxel and a stabilizing agent, wherein stability of the composition is enhanced as compared to that of a composition without the stabilizing agent. In some embodiments, the stabilizing agent is a chelating agent, such as any of (and in some embodiments selected from the group consisting of) edetate, citrate, malic acid, pentetate, tromethamine, derivatives thereof, and mixtures thereof. In some embodiments, the stabilizing agent is a citrate or a derivative thereof (such as sodium citrate). In some embodiments, the composition comprises sodium citrate and sodium chloride. In some embodiments, the stabilizing agent is an edetate or a derivative thereof (such as EDTA). In some embodiments, the stabilizing agent is sodium gluconate. In some embodiments, the stabilizing agent is sodium pyrophosphate.

In some embodiments, the composition comprises (1) particles (such as nanoparticles) comprising (in various embodiments consisting of or consisting essentially of) a poorly water soluble pharmaceutical agent and biocompatible polymer (such as a carrier protein, which may be albumin such as HSA); and (2) a stabilizing agent, wherein stability of the composition is enhanced as compared to that of a composition without the stabilizing agent. In some embodiments, the composition comprises particles (such as nanoparticles) comprising (in various embodiments consisting of or consisting essentially of) (1) docetaxel and biocompatible polymer (such as carrier protein, which may be albumin such as HSA); and (2) a stabilizing agent, wherein stability of the composition is enhanced as compared to that of a composition without the stabilizing agent. In some embodiments, the docetaxel is coated with the biocompatible polymer (such as carrier protein). In some embodiments, the stabilizing agent is a chelating agent, such as any of (and in some embodiments selected from the group consisting of) edetate, citrate, malic acid, pentetate, tromethamine, derivatives thereof, and mixtures thereof. In some embodiments, the stabilizing agent is a citrate or a derivative thereof (such as sodium citrate). In some embodiments, the composition comprises sodium citrate and sodium chloride. In some embodiments, the stabilizing agent is an edetate or a derivative thereof (such as EDTA). In some embodiments, the stabilizing agent is a malic acid. In some embodiments, the stabilizing agent is sodium gluconate. In some embodiments, the stabilizing agent is sodium pyrophosphate.

In some embodiments, the composition comprises (1) particles (such as nanoparticles) comprising (in various embodiments consisting of or consisting essentially of) a poorly water soluble pharmaceutical agent and albumin; and (2) a stabilizing agent, wherein the weight ratio of the albumin to the poorly water soluble pharmaceutical agent in the composition is about 0.01:1 to about 100:1, and wherein stability of the composition is enhanced as compared to that of a composition without the stabilizing agent. In some embodiments, the poorly water soluble agent is coated with albumin. In some embodiments, the composition comprises (1) particles (such as nanoparticles) comprising (in various embodiments consisting of or consisting essentially of) a poorly water soluble pharmaceutical agent and albumin; and (2) a stabilizing agent, wherein the weight ratio of the albumin to the poorly water soluble pharmaceutical agent in the composition is about 18:1 or less (including for example any of about 1:1 to about 18:1, about 2:1 to about 15:1, about 3:1 to about 12:1, about 4:1 to about 10:1, and about 9:1), and wherein stability of the composition is enhanced as compared to that of a composition without the stabilizing agent. In some embodiments, the poorly water soluble agent is coated with albumin.

In some embodiments, the composition comprises (1) particles (such as nanoparticles) comprising (in various embodiments consisting of or consisting essentially of) docetaxel and albumin; and (2) a stabilizing agent, wherein the weight ratio of albumin and the docetaxel in the composition is about 0.01:1 to about 100:1, and wherein stability of the composition is enhanced as compared to that of a composition without the stabilizing agent. In some embodiments, the composition comprises (1) particles (such as nanoparticles) comprising (in various embodiments consisting of or consisting essentially of) docetaxel and albumin; and (2) a stabilizing agent, wherein the weight ratio of albumin and the docetaxel in the composition is about 18:1 or less (including for example any of about 1:1 to about 18:1, about 2:1 to about 15:1, about 3:1 to about 12:1, about 4:1 to about 10:1, and about 9:1), and wherein stability of the composition is enhanced as compared to that of a composition without the stabilizing agent. In some embodiments, the docetaxel is coated with albumin. In some embodiments, the composition is substantially free (such as free) of surfactant. In some embodiments, the composition comprises a stable aqueous suspension of particles (such as nanoparticles) comprising docetaxel and albumin (such as particles of docetaxel coated with albumin), wherein the composition further comprises a stabilizing agent, wherein the weight ratio of albumin and the docetaxel in the composition is about 18:1 or less (including for example about 1:1 to about 18:1, about 2:1 to about 15:1, about 3:1 to about 12:1, about 4:1 to about 10:1, and about 9:1), and wherein stability of the composition is enhanced as compared to that of a composition without the stabilizing agent. In some embodiments, the composition comprises a dry (such as lyophilized) composition that can be reconstituted, resuspended, or rehydrated to form generally a stable aqueous suspension of particles (such as nanoparticles) comprising docetaxel and albumin (such as docetaxel coated with albumin), wherein the composition further comprises a stabilizing agent, wherein the weight ratio of albumin and the docetaxel in the composition is about 18:1 or less (including for example any of about 1:1 to about 18:1, about 2:1 to about 15:1, about 3:1 to about 12:1, about 4:1 to about 10:1, and about 9:1), and wherein stability of the composition is enhanced as compared to that of a composition without the stabilizing agent. In some embodiments, the stabilizing agent is a chelating agent, such as any of (and in some embodiments selected from the group consisting of) edetate, citrate, malic acid, pentetate, tromethamine, derivatives thereof, and mixtures thereof. In some embodiments, the stabilizing agent is a citrate or a derivative thereof (such as sodium citrate). In some embodiments, the composition comprises sodium citrate and sodium chloride. In some embodiments, the stabilizing agent is an edetate or a derivative thereof (such as EDTA). In some embodiments, the stabilizing agent is sodium gluconate. In some embodiments, the stabilizing agent is sodium pyrophosphate.

In some embodiments, the particles (such as nanoparticles) in the composition have an average or mean diameter of no greater than about any of 1000, 900, 800, 700, 600, 500, 400, 300, 200, and 100 nm. In some embodiments, the average or mean diameter of the particles is between about 20 to about 400 nm. In some embodiments the average or mean diameter of the particles is between about 40 to about 200 nm. In some embodiments, the particles or droplets are sterile-filterable.

The compositions described herein may be a stable aqueous suspension of the poorly water soluble pharmaceutical agent, such as a stable aqueous suspension of the poorly water soluble pharmaceutical agent at a concentration of any of about 0.1 to about 100 mg/ml, including for example about 0.1 to about 50 mg/ml, about 0.1 to about 20 mg/ml, about 1 to about 15 mg/ml, about 1 to about 10 mg/ml, about 2 to about 8 mg/ml, about 4 to about 6 mg/ml, and about 5 mg/ml. In some embodiments, the concentration of the poorly water soluble pharmaceutical agent is at least about any of 1 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, and 50 mg/ml.

In some embodiments, the composition is a dry (such as lyophilized) composition that can be reconstituted, resuspended, or rehydrated generally to form a stable aqueous suspension of the poorly water soluble pharmaceutical agent. In some embodiments, the composition is a liquid (such as aqueous) composition obtained by reconstituting or resuspending a dry composition. In some embodiments, the composition is an intermediate liquid (such as aqueous) composition that can be dried (such as lyophilized).

In some embodiments, the composition is suitable for parenteral (such as intravenous) administration. In some embodiments, the composition is suitable for multidose administration. In some embodiments, the composition is sterile filterable. In some embodiments, the composition does not cause significant side effects in an individual (such as human) when administered to the individual. In some embodiments, the compositions described herein are substantially free (such as free) of surfactants. The stabilizing agent containing compositions described herein may further comprise a sugar (including, for example, sucrose, mannitol, fructose, lactose, maltose, and trehalose) or other lyophilization or reconstitution aids.

In some embodiments, the amount of the stabilizing agent in the composition is below the level that induces a toxicological effect (i.e., above a clinically acceptable level of toxicity) or is at a level where a potential side effect can be controlled or tolerated when the composition is administered to an individual.

In another aspect, there are provided compositions (such as pharmaceutical composition) comprising docetaxel, wherein the docetaxel used for preparation of the composition is in anhydrous form (for example the docetaxel may be anhydrous prior to being incorporated into the composition). In some embodiments, the composition further comprises a stabilizing agent (such as the stabilizing agents described herein). Compositions which include use of anhydrous docetaxel are further described in a section below.

In some embodiments, the composition comprises docetaxel and a biocompatible polymer (such as a carrier protein, for example, albumin), wherein the docetaxel used for preparation of the composition is in anhydrous form. In some embodiments, the composition comprises particles (such as nanoparticles) comprising docetaxel and a biocompatible polymer (such as a carrier protein, for example albumin), wherein the docetaxel used for preparation of the composition is in anhydrous form.

In some embodiments, the composition comprises nanoparticles comprising docetaxel and albumin, wherein the docetaxel used for preparation of the composition is in anhydrous form. In some embodiments, the weight ratio of albumin and docetaxel in the composition is less than about 18:1, including for example any of about 1:1 to about 18:1, about 2:1 to about 15:1, about 3:1 to about 12:1, about 4:1 to about 10:1, about 9:1. In some embodiments, the docetaxel is coated with albumin. In some embodiments, the nanoparticles in the composition have an average or mean particle size of no greater than about 200 nm. In some embodiments, the particles in the composition are sterile filterable. In some embodiments, the nanoparticles in the compositions have two or more of these properties.

In some embodiments, the composition comprises docetaxel and a surfactant, wherein the docetaxel used for preparation of the composition is in anhydrous form. In some embodiments, the surfactant used in preparation of the composition is anhydrous. In some embodiments, the surfactant is a polysorbate (such as Tween 80). In some embodiments, the surfactant is Cremophor. In some embodiments, the composition further comprises a stabilizing agent (such as the stabilizing agents described herein).

The compositions prepared with anhydrous docetaxel may be dry (such as lyophilized) compositions. In some embodiments, the composition is a liquid (such as aqueous) composition obtained by reconstituting or resuspending a dry composition. In some embodiments, the composition is an intermediate liquid (such as aqueous) composition that can be dried (such as lyophilized).

Also provided are unit dosage forms of compositions described herein, articles of manufacture comprising the inventive compositions or unit dosage forms in suitable packaging (such as vials or vessels (including sealed vials or vessels and sterile sealed vials or vessels)), and kits comprising the compositions. The invention also provides methods of making the compositions as described herein.

Also provided are methods of stabilizing a poorly water soluble pharmaceutical agent in a composition. In some embodiments, there is provided a method of stabilizing a poorly water soluble pharmaceutical agent in a composition (such as a nanoparticle composition), comprising combining the composition (such as nanoparticle composition) comprising a poorly water soluble pharmaceutical agent with a stabilizing agent, wherein the resultant composition is stable under the same condition under which the composition is unstable prior to the addition of the stabilizing agent. In some embodiments, the method further comprises identifying and selecting a composition that is unstable under one or more conditions. In some embodiments, the composition for selection comprises a poorly water soluble pharmaceutical agent and a carrier protein (such as albumin).

Methods of using the compositions described herein are also provided. For example, in some embodiments, there is provided a method of treating cancer in an individual (such as human), comprising administering to the individual an effective amount of a composition comprising a poorly water soluble antineoplastic agent, a carrier protein (such as albumin), and a stabilizing agent, wherein stability of the composition is enhanced as compared to that of a composition without the stabilizing agent. In some embodiments, there is provided a method of treating cancer in an individual (such as human), comprising administering to the individual an effective amount of a composition comprising docetaxel, a carrier protein (such as albumin), and a stabilizing agent, wherein stability of the composition is enhanced as compared to that of a composition without the stabilizing agent. In some embodiments, the composition comprises particles (such as nanoparticles) comprising docetaxel and carrier protein. In some embodiments, the composition comprises particles (such as nanoparticles) comprising docetaxel and albumin (such as albumin-comprising nanoparticle formulations of docetaxel or Nab-docetaxel). In some embodiments, the composition comprises Nab-docetaxel and citrate. In some embodiments, the composition comprises Nab-docetaxel, citrate, and sodium chloride (such as about 200 mM sodium chloride and about 300 mM sodium citrate). In some embodiments, the cancer is any of: prostate cancer, colon cancer, head and neck cancer, breast cancer, pancreatic cancer, lung cancer, and ovarian cancer. In some embodiments, the cancer is solid tumor. In some embodiments, the composition is administered at least about any of once every three weeks, once every two weeks, once a week, twice a week, three times a week, four times a week, five times a week, six times a week, or daily. In some embodiments, the composition is administered (with or without breaks) for at least about any of 1, 2, 3, 4, 5, 6, 7, 8, 9, 10, 11, 12, or more month(s). In some embodiments, the composition is administered via any of intravenous, intraarterial, oral, topical, or inhalational routes.

General reference to "the compositions" or "compositions" includes and is applicable to compositions of the invention. The invention also provides pharmaceutical compositions comprising the components described herein.

Reference to docetaxel herein applies to docetaxel or its derivatives (or analogs) and accordingly the invention contemplates and includes both these embodiments. Reference to "docetaxel" is to simplify the description and is exemplary. Derivatives or analogs of docetaxel include, but are not limited to, compounds that are structurally similar to docetaxel or are in the same general chemical class as docetaxel, e.g., taxanes. In some embodiments, the derivative or analog of docetaxel retains similar biological, pharmacological, chemical and/or physical property (including, for example, functionality) of docetaxel. Examples of docetaxel derivatives or analogs include paclitaxel and ortataxel. This same principle of description applies to other agents provided herein such as including, for example, stabilizing agents and poorly water soluble pharmaceutical agents (such as taxane (including paclitaxel, ortataxel, or other taxanes), geldanamycin, 17-allyl amino geldanamycin, thiocolchicine and its dimers, rapamycin, cyclosporine, epothilone, radicicol, and combretastatin).

It is understood that aspects and embodiments of the invention described herein include "consisting" and/or "consisting essentially of" aspects and embodiments.

Stabilizing Agents

Various compositions described herein comprise a stabilizing agent. "Stabilizing agent" used herein refers to an agent that enhances the stability of the composition as compared to a composition without addition of the stabilizing agent. In some embodiments, the stability of the stabilizing agent-containing composition is at least about 1.5× (including for example at least about any of 2×, 3×, 4×, 5×, 6, 7×, 8×, 9×, 10×, 15×, 20×, 25×, 30×, or more) greater as compared to that of a composition without the stabilizing agent.

As described above, stability of a composition can be evaluated by the ability of the poorly water soluble pharmaceutical agent to remain non-precipitated or non-sedimented (for example based on visual observation and/or microscopic observation) in a liquid suspension over a certain period of time. Stability of a dry (such as a lyophilized) composition can be evaluated based on the behavior of the liquid suspension resulting from reconstitution or rehydration of the dry composition.

In some embodiments, the stabilizing agent delays or prevents precipitation or sedimentation of the poorly water soluble pharmaceutical agent in a liquid suspension. In some embodiments, the stabilizing agent delays or prevents crystallization of the poorly water soluble pharmaceutical agent in the composition. In some embodiments when the composition comprises particles of poorly water soluble agents, the stabilizing agent may prevent or delay changes of particle sizes in the composition.

The stabilizing agents are particularly useful for compositions that would otherwise exhibit significant instability. For example, in some embodiments, the composition prior to the addition of the stabilizing agent is stable for less than about 24 hours (including for example less than about any of 12, 10, 8, 6, 4, or 2 hours). In some embodiments, the poorly water soluble pharmaceutical agent in a liquid suspension prior to the addition of the stabilizer precipitates or sediments in less than about 24 hours (including for example less than about any of 12, 10, 8, 6, 4, or 2 hours). In some embodiments, the composition prior to the addition of the stabilizing agent precipitates or sediments in less than about 24 hours when the concentration of the poorly water soluble pharmaceutical agent is more than about 0.1 mg/ml (including for example more than about any of 0.5 mg/ml, 1 mg/ml, 1.3 mg/ml, 1.5 mg/ml, 2 mg/ml, 3 mg/ml, 4 mg/ml, 5 mg/ml, or 10 mg/ml).

In some embodiments, the composition prior to the addition of the stabilizing agent precipitates or sediments upon dilution of the composition for parental administration. Addition of stabilizing agent to those compositions allows the compositions to remain stable (for example not precipitate or sediment) under similar conditions. Accordingly, in some embodiments, there is provided a composition comprising a poorly water soluble pharmaceutical agent and a stabilizing agent, wherein the composition (such as a nanoparticle composition) is stable under the same condition under which the composition without the stabilizing agent is unstable. In some embodiments, the stabilizing agent delays or prevents precipitation or sedimentation of the poorly water soluble pharmaceutical agent in a liquid suspension of a composition under a condition where the poorly water soluble pharmaceutical agent would otherwise precipitate or sediment.

Suitable stabilizing agents include but are not limited to sodium citrate (all forms, 0.01-20% w/v), sodium pyrophosphate (0.1-10% w/v), EDTA (all forms, 0.01-20%), pentetate (all forms, 0.01-20%), sodium gluconate (0.1-10% w/v) and suitable combinations thereof. The weight percentage (w/v) refers to the percentage of the stabilizing agent in a liquid composition, or, in the case of a solid composition, the weight percentage (w/v) of the stabilizing agent upon reconstitution or rehydration. The stabilizing agent should be used in an amount sufficient to increase the stability of the formulation. Preferably, the amount of the stabilizing agent used will provide a stable composition that does not show evidence of precipitation or sedimentation for at least about 8 hours, more preferably at least about 24 hours after reconstitution or rehydration, more preferably for at least about 48 hours, most preferably for at least about 72 hours.

In some embodiments, the stabilizing agent is a chelating agent. These chelating agents are either specific to a particular metal ion (such as calcium, zinc, magnesium, etc.), or show a broad spectrum of metal ion specificity. In some embodiments, the chelating agent is a polydentate. In some embodiments, the chelating agent comprises one or more carboxylic acid groups. In some embodiments, the chelating agent is not deferoxamine. Suitable chelating agents include, but are not limited to, edetate, citrate, malic acid, pentetate, tromethamine, and derivatives thereof.

One stabilizing agent contemplated herein is an edetate, i.e., ethylenediaminetetraacetic acid (EDTA) and derivatives thereof. Suitable edetates include disodium edetate, trisodium edetate, tetrasodium edetate and disodium calcium edetate. In some embodiments, the edetate is present in the compositions in a concentration of about 0.01 mg/ml to about 200 mg/ml, including for example about 0.05 mg/ml to about 150 mg/ml, about 0.1 mg/ml to about 100 mg/ml, about 0.2 to about 50 mg/ml, about 0.5 mg/ml to about 20 mg/ml, about 1 mg/ml to about 10 mg/ml, and about 1 mg/ml to about 5 mg/ml. In some embodiments, the weight ratio of the edetate and the poorly water soluble pharmaceutical agent (such as docetaxel) in the composition is about 0.002:1 to about 40:1, including for example about 0.01:1 to about 30:1, about 0.02:1 to about 20:1, about 0.04:1 to about 10:1, about 0.1:1 to about 4:1, about 0.2:1 to about 2:1, about 0.2:1 to about 1:1.

Another stabilizing agent contemplated herein is citrate or a derivative thereof (i.e., citric acid or derivatives thereof), such as sodium citrate. Suitable concentrations of citrate include, for example, about 0.1 mg/ml to about 200 mg/ml, including for example any of about 0.2 mg/ml to about 100 mg/ml, about 0.3 mg/ml to about 50 mg/ml, about 0.5 mg/ml to about 10 mg/ml, and about 1 mg/ml to about 5 mg/ml. In some embodiments, the concentration of citrate is less than about 200 mg/ml, such as less than about any of 100, 50, 30, 20, 10, 9, 8, 7, 6, 5, 4, 3, 2, 1, 0.9, 0.8, 0.7, 0.6, 0.5, 0.4, 0.3, or 0.2 mg/ml. In some embodiments, the weight ratio of the citrate and the poorly water soluble pharmaceutical agent (such as citrate) in the composition is about 0.02:1 to about 40:1, including for example any of about 0.04:1 to about 20:1, about 0.06:1 to about 10:1, about 0.1:1 to about 2:1, and about 0.2:1 to about 1:1. In some embodiments, the weight ratio of the citrate and the poorly water soluble pharmaceutical agent in the composition is less than about any of 20:1, 10:1, 8:1, 5:1, 2:1, 1:1, 0.8:1, 0.5:1, 0.2:1, and 0.1:1.

Any form of citrate is acceptable for use in the present invention, and include, for example, citric acid and sodium citrate. Sodium citrate is particularly preferred. When sodium citrate is utilized, suitable concentrations include from about 1 to 600 mM. When citrate and sodium chloride are utilized, suitable concentrations include from about 1 to 600 mM and 1 to 1000 mM, respectively. In some embodiments, the concentrations of citrate and sodium chloride are about 50 to about 200 mM and about 300 to about 500 mM, respectively. In some embodiments, the composition comprises about 50 mM citrate (such as sodium citrate) and about 500 mM sodium chloride. In some embodiments, the composition comprises about 200 mM citrate (such as sodium citrate) and about 300 mM sodium chloride. In some embodiments, the composition is a dry (such as lyophilized) composition, wherein the weight ratio of the citrate to docetaxel in the composition is about 17:1 and, when sodium chloride is present, the weight ratio of the sodium chloride to docetaxel is about 3.5:1. In other embodiments, the stabilizing agent is not a citrate (i.e., other than citrate).

The stabilizing agent can also be a pentetate (including calcium trisodium pentetate). In some embodiments, the amount of pentetate is in a concentration of about 0.01 mg/ml to about 200 mg/ml, including for example any of about 0.05 mg/ml to about 150 mg/ml, about 0.1 mg/ml to about 100 mg/ml, about 0.2 to about 50 mg/ml, about 0.5 mg/ml to about 20 mg/ml, about 1 mg/ml to about 10 mg/ml, and about 1 mg/ml to about 5 mg/ml. In some embodiments, the weight ratio of the pentetate and the poorly water soluble pharmaceutical agent (such as docetaxel) in the composition is about 0.002:1 to about 40:1, including for example any of about 0.01:1 to about 30:1, about 0.02:1 to about 20:1, about 0.04:1 to about 10:1, about 0.1:1 to about 4:1, about 0.2:1 to about 2:1, about 0.2:1 to about 1:1.

Another stabilizing agent contemplated herein is tromethamine. Tromethamine as used herein, refers to 2-amino-2-hydroxymethyl-1,3-propanediol, also known as TRIS. In some embodiments, tromethamine is in a concentration of about 0.1 mg/ml to about 100 mg/ml, including for example about 0.5 mg/ml to about 50 mg/ml, about 1 mg/ml to about 10 mg/ml, and about 2 mg/ml to about 5 mg/ml. In some embodiments, the weight ratio of the tromethamine and the poorly water soluble pharmaceutical agent in the composition is about 0.02:1 to about 20:1, including for example 0.1:1 to about 10:1, about 0.2:1 to about 2:1, and about 0.4:1 to about 1:1.

Other suitable metal chelating stabilizing agents and their exemplary amount include, but are not limited to, potassium sorbate (0.5 mg/ml), sodium ascorbate (1 mg/ml), sodium formaldehyde sulfoxylate (0.1 mg/ml), and monothiolglycerol (5 mg/ml).

In some embodiments, the stabilizing agent is sodium pyrophosphate. Suitable concentration of sodium pyrophosphate include any of about 0.1 to about 10% (w/v), about 0.5 to about 5%, and about 1 to about 2%. In some embodiments, the weight ratio of the sodium pyrophosphate and the poorly water soluble pharmaceutical agent in the composition is any of about 0.2:1 to about 20:1, about 1:1 to about 10:1, about 2:1 to about 4:1.

In some embodiments, the stabilizing agent is sodium gluconate. Suitable concentration of sodium gluconate include any of about 0.1 to about 10% (w/v), about 0.5 to about 5%, and about 1 to about 2%. In some embodiments, the weight ratio of the sodium gluconate and the poorly water soluble pharmaceutical agent in the composition is any of about 0.2:1 to about 20:1, about 1:1 to about 10:1, about 2:1 to about 4:1.

In some embodiments, the compositions described herein comprise at least two (including for example at least any of 2, 3, 4, 5, 6, 7, 8, 9, or 10) different stabilizing agents (such as stabilizing agents described herein).

Poorly Water Soluble Pharmaceutical Agents

The compositions described herein comprise poorly water soluble pharmaceutical agents. For example, the solubility in water of the poorly water soluble agent at 20-25° C. may be less than about 10 mg/ml, including for example less than about any of 5, 2, 1, 0.5, 0.2, 0.1, 0.05, 0.02, and 0.01 mg/ml.

Poorly water soluble pharmaceutical agents contemplated for use in the practice of the present invention include poorly water soluble pharmaceutically active agents, diagnostic agents, agents of nutritional value and the like. Poorly water soluble pharmaceutical agents can be, for example, analgesics/antipyretics, anesthetics, antiasthmatics, antibiotics, antidepressants, antidiabetics, antifungal agents, antihypertensive agents, anti-inflammatories, antineoplastics, antianxiety agents, immunosuppressive agents, antimigraine agents, sedatives, antianginal agents, antipsychotic agents, antimanic agents, antiarrhythmics, antiarthritic agents, antigout agents, anticoagulants, thrombolytic agents, antifibrinolytic agents, hemorheologic agents, antiplatelet agents, anticonvulsants, antiparkinson agents, antihistamines/antipruritics, agents useful for calcium regulation, antibacterial agents, antiviral agents, antimicrobials, anti-infectives, bronchodialators, hormones, hypoglycemic agents, hypolipidemic agents, antiulcer/antireflux agents, antinauseants/antiemetics, oil-soluble vitamins (e.g., vitamins A, D, E, K, and the like).

In some embodiments, the poorly water soluble pharmaceutical agent is an antineoplastic agent. In some embodiments, the poorly water soluble pharmaceutical agent is a chemotherapeutic agent.

Suitable poorly water soluble pharmaceutical agents include, but are not limited to, taxanes (such as paclitaxel, docetaxel, ortataxel and other taxanes), epothilones, camptothecins, colchicines, geladanamycins, amiodarones, thyroid hormones, amphotericin, corticosteroids, propofol, melatonin, cyclosporine, rapamycin (sirolimus) and derivatives, tacrolimus, mycophenolic acids, ifosfamide, vinorelbine, vancomycin, gemcitabine, SU5416, thiotepa, bleomycin, diagnostic radiocontrast agents, and derivatives thereof. Other poorly water soluble pharmaceutical agents that are useful in the inventive compositions are described in, for example, U.S. Pat. Nos. 5,916,596, 6,096,331, 6,749,868, and 6,537,539. Additional examples of poorly water soluble pharmaceutical agents include those compounds which are poorly water soluble and which are listed in the "Therapeutic Category and Biological Activity Index" of The Merck Index (12$^{th}$ Edition, 1996).

In some embodiments, the poorly water soluble pharmaceutical agent is any of (and in some embodiments selected from the group consisting of) paclitaxel, docetaxel, ortataxel or other taxane or taxane analog, 17-allyl amino geldanamycin (17-AAG), 18-derivatized geldanamycin, camptothecin, propofol, amiodarone, cyclosporine, epothilone, radicicol, combretastatin, rapamycin, amphotericin, liothyronine, epothilone, colchicine, thiocolchicine and its dimers, thyroid hormone, vasoactive intestinal peptide, corticosteroids, melatonin, tacrolimus, mycophenolic acids, epothilones, radicicols, combretastatins, and analog or derivative thereof. In some embodiments, the poorly water soluble pharmaceutical agent is any of (and in some embodiments selected from the group consisting of) paclitaxel, docetaxel, ortataxel or other taxanes, geldanamycin, 17-allyl amino geldanamycin, thiocolchicine and its dimers, rapamycin, cyclosporine, epothilone, radicicol, and combretastatin. In some embodiments, the poorly water soluble pharmaceutical agent is rapamycin. In some embodiments, the poorly water soluble pharmaceutical agent is 17-AAG. In some embodiments, the poorly water soluble pharmaceutical agent is a thiocolchicine dimer (such as IDN5404).

In some embodiments, the poorly water soluble pharmaceutical agent is a taxane or derivative thereof, which includes, but is not limited to, paclitaxel, docetaxel and IDN5109 (ortataxel), or a derivative thereof. In some embodiments, the composition comprises a non-crystalline and/or amorphous taxane (such as paclitaxel or a derivative thereof). In some embodiments, the composition is prepared by using an anhydrous taxane (such as anhydrous docetaxel or a derivative thereof).

In some embodiments, the poorly water soluble pharmaceutical agent is docetaxel or a derivative thereof. In some embodiments, the docetaxel in the composition is noncrystalline or amorphous. In some embodiments, the docetaxel is in any one or more of the following forms: anhydrate, hemihydrate, dihydrate, and trihydrate forms. Anhydrous docetaxel has been shown to produce more stable formulation than those made with a hydrated docetaxel such as docetaxel trihydrate or hemi-hydrate, and is particularly useful for the preparation of the docetaxel compositions described herein.

Biocompatible Polymers and Carrier proteins

The compositions described herein may also comprise biocompatible polymers, such as carrier proteins further described herein.

As used herein, the term "biocompatible" describes a substance that does not appreciably alter or affect in any adverse way, the biological system into which it is introduced. Biocompatible polymer includes naturally-occurring or synthetic biocompatible materials such as proteins, polynucleotides, polysaccharides (e.g., starch, cellulose, dextrans, alginates, chitosan, pectin, hyaluronic acid, and the like), and lipids. Suitable biocompatible polymers include, for example, naturally occurring or synthetic proteins such as albumin, insulin, hemoglobin, lysozyme, immunoglobulins, α-2-macroglobulin, fibronectin, vitronectin, fibrinogen, casein and the like, as well as combinations of any two or more thereof. Synthetic polymers include, for example, poly-alkylene glycols (e.g., linear or branched chain), polyvinyl alcohol, polyacrylates, polyhydroxyethyl methacrylate, polyacrylic acid, polyethyloxazoline, polyacrylamides, polyisopropyl acrylamides, polyvinylpyrrolidone, polylactide/glycolide and the like, and combinations thereof.

The term "proteins" refers to polypeptides or polymers of amino acids of any length (including full length or fragments), which may be linear or branched, comprise modified amino acids, and/or be interrupted by non-amino acids. The term also encompasses an amino acid polymer that has been modified naturally or by intervention; for example, disulfide bond formation, glycosylation, lipidation, acetylation, phosphorylation, or any other manipulation or modification. Also included within this term are, for example, polypeptides containing one or more analogs of an amino acid (including, for example, unnatural amino acids, etc.), as well as other modifications known in the art. The proteins described herein may be naturally-occurring, i.e., obtained or derived from a natural source (such as blood), or synthesized (such as chemically synthesized or by synthesized by recombinant DNA techniques).

Examples of suitable proteins include proteins normally found in blood or plasma, which include, but are not limited to, albumin, immunoglobulin including IgA, lipoproteins, apolipoprotein B, α-acid glycoprotein, β-2-macroglobulin, thyroglobulin, transferrin, fibronectin, factor VII, factor VIII, factor IX, factor X, and the like. In some embodiments, the carrier protein is non-blood protein, such as casein, α-lactalbumin, β-lactoglobulin. The proteins may either be natural in origin or synthetically prepared. In some embodiments, the protein is albumin, such as HSA. HSA is a highly soluble globular protein of $M_r$ 65K and consists of 585 amino acids. HSA is the most abundant protein in the plasma and accounts for 70-80% of the colloid osmotic pressure of human plasma. The amino acid sequence of HSA contains a total of 17 disulphide bridges, one free thiol (Cys 34), and a single tryptophan (Trp 214). Intravenous use of HSA solution has been indicated for the prevention and treatment of hypovolumic shock (see, e.g., Tullis, *JAMA*, 237, 355-360, 460-463, (1977)) and Houser et al., *Surgery, Gynecology and Obstetrics*, 150, 811-816 (1980)) and in conjunction with exchange transfusion in the treatment of neonatal hyperbilirubinemia (see, e.g., Finlayson, *Seminars in Thrombosis and Hemostasis*, 6, 85-120, (1980)). Other albumins are contemplated, such as bovine serum albumin. Use of such non-human albumins could be appropriate, for example, in the context of use of these compositions in non-human mammal, such as the veterinary animals (including domestic pets and agricultural animals).

Human serum albumin (HSA) has multiple hydrophobic binding sites (a total of eight for fatty acids, an endogenous ligand of HSA) and binds a diverse set of pharmaceutical agents, especially neutral and negatively charged hydrophobic compounds (Goodman et al., *The Pharmacological Basis of Therapeutics*, 9$^{th}$ ed, McGraw-Hill New York (1996)). Two high affinity binding sites have been proposed in subdomains IIA and IIIA of HSA, which are highly elongated hydrophobic pockets with charged lysine and arginine residues near the surface which function as attachment points for polar ligand features (see, e.g., Fehske et al., *Biochem. Pharmcol.*, 30, 687-92 (1981), Vorum, *Dan. Med. Bull.*, 46, 379-99 (1999), Kragh-Hansen, *Dan. Med. Bull.*, 1441, 131-40 (1990), Curry et al., *Nat. Struct. Biol.*, 5, 827-35 (1998), Sugio et al., *Protein. Eng.*, 12, 439-46 (1999), He et al., *Nature*, 358, 209-15 (1992), and Carter et al., *Adv. Protein. Chem.*, 45, 153-203 (1994)). Paclitaxel and propofol have been shown to bind HSA (see, e.g., Paal et al., *Eur. J. Biochem.*, 268(7), 2187-91 (2001), Purcell et al., *Biochim. Biophys. Acta*, 1478(1), 61-8 (2000), Altmayer et al., *Arzneimittelforschung*, 45, 1053-6

(1995), and Gamido et al., *Rev. Esp. Anestestiol. Reanim.*, 41, 308-12 (1994)). In addition, docetaxel has been shown to bind to human plasma proteins (see, e.g., Urien et al., *Invest. New Drugs*, 14(2), 147-51 (1996)).

To provide an example, carrier proteins are further described below. It is understood that this description generally applies to biocompatible polymers.

The carrier protein (such as albumin) in the composition generally serves as a carrier for the poorly water soluble pharmaceutical agent, i.e., the carrier protein in the composition makes the poorly water soluble pharmaceutical agent more readily suspendable in an aqueous medium or helps maintain the suspension as compared to compositions not comprising a carrier protein. This can avoid the use of toxic solvents for solubilizing the poorly water soluble pharmaceutical agent, and thereby can reduce one or more side effects of administration of the poorly water soluble pharmaceutical agent into an individual (such as a human). Thus, in some embodiments, the composition described herein is substantially free (such as free) of surfactants (such as Tween 20). A composition is "substantially free of surfactant" if the amount of surfactant in the composition is not sufficient to cause one or more side effect(s) in an individual when the composition is administered to the individual.

In some embodiments, the carrier protein is associated with the poorly water soluble pharmaceutical agent, i.e., the composition comprises carrier protein-associated poorly water soluble pharmaceutical agent. "Association" or "associated" is used herein in a general sense and refers to the carrier protein affecting the behavior and/or property of the poorly water soluble pharmaceutical agent in an aqueous composition. For example, the carrier protein and the poorly water soluble pharmaceutical agent are considered as being "associated" if the carrier protein makes the poorly water soluble pharmaceutical agent more readily suspendable in an aqueous medium as compared to a composition without the carrier protein. As another example, the carrier protein and the poorly water soluble pharmaceutical agent is associated if the carrier protein stabilizes the poorly water soluble pharmaceutical agent in an aqueous suspension. For example, the carrier protein and the poorly water soluble pharmaceutical agent can be present in a particle or a nanoparticle, which are further described herein.

A poorly water soluble pharmaceutical agent is "stabilized" by a carrier protein in an aqueous suspension if it remains suspended in an aqueous medium (such as without visible precipitation or sedimentation) for an extended period of time, such as for at least about any of 0.1, 0.2, 0.25, 0.5, 1, 2, 3, 4, 5, 6, 7, 8, 9, 10, 11, 12, 24, 36, 48, 60, or 72 hours. The suspension is generally, but not necessarily, suitable for administration to an individual (such as human). As described above, stability of the suspension is in some embodiments evaluated at room temperature (such as 20-25° C.) or refrigerated conditions (such as 4° C.). Stability can also be evaluated under accelerated testing conditions, such as at a temperature that is higher than about 40° C. As described above, the stability of the suspension can further be enhanced by addition of the stabilizing agents described herein.

The carrier protein and the poorly water soluble pharmaceutical agent in the composition can be associated in various manners. For example, in some embodiments, the carrier protein is in admixture with the poorly water soluble pharmaceutical agent. In some embodiments, the carrier protein encapsulates or entraps the poorly water soluble pharmaceutical agent. In some embodiments, the carrier protein is bound (such as non-covalently bound) to the poorly water soluble pharmaceutical agent. In some embodiments, the composition may exhibit one or more of the above aspects.

In some embodiments, the composition comprises particles (such as nanoparticles) comprising (in various embodiments consisting essentially of) a poorly water soluble pharmaceutical agent and a carrier protein. When the poorly water soluble pharmaceutical agent is in a liquid form, the particles or nanoparticles are also referred to as droplets or nanodroplets. In some embodiments, the poorly water soluble agent is coated with the carrier protein. Particles (such as nanoparticles) of poorly water soluble pharmaceutical agents have been disclosed in, for example, U.S. Pat. Nos. 5,916,596; 6,506,405; and 6,537,579 and also in U.S. Pat. App. Pub. No. 2005/0004002A1.

In some embodiments, the composition comprises particles (such as nanoparticles) with an average or mean diameter of no greater than about 1000 nanometers (nm), such as less than about any of 900, 800, 700, 600, 500, 400, 300, 200, and 100 nm. In some embodiments, the average or mean diameter of the particles is no greater than about 200 nm. In some embodiments, the average or mean diameter of the particles is between about 20 to about 400 nm. In some embodiments, the average or mean diameter of the particles is between about 40 to about 200 nm. In some embodiments, the nanoparticles in the composition have an average or mean particle size of no greater than about 200 nm. In some embodiments, the particles are sterile-filterable.

The particles (such as nanoparticles) described herein may be present in a dry formulation (such as lyophilized composition) or suspended in a biocompatible medium. Suitable biocompatible media include, but are not limited to, water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, lipid-containing emulsions, and the like.

The amount of carrier protein in the composition described herein will vary depending on the poorly water soluble pharmaceutical agent and other components in the composition. In some embodiments, the composition comprises a carrier protein in an amount that is sufficient to stabilize the poorly water soluble pharmaceutical agent in an aqueous suspension, for example, in the form of a stable colloidal suspension (such as a stable suspension of nanoparticles). In some embodiments, the carrier protein is in an amount that reduces the sedimentation rate of the poorly water soluble pharmaceutical agent in an aqueous medium. For particle-containing compositions, the amount of the carrier protein also depend on the size and density of particles of the poorly water soluble pharmaceutical agent.

In some embodiments, the carrier protein is present in an amount that is sufficient to stabilize the poorly water soluble pharmaceutical agent in an aqueous suspension at a certain concentration. For example, the concentration of the poorly water soluble pharmaceutical agent in the composition is about 0.1 to about 100 mg/ml, including for example any of about 0.1 to about 50 mg/ml, about 0.1 to about 20 mg/ml, about 1 to about 10 mg/ml, about 2 to about 8 mg/ml, and about 4 to about 6 mg/ml. In some embodiments, the concentration of the poorly water soluble pharmaceutical agent is at least about any of 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, and 50 mg/ml. In some embodiments, the carrier protein is present in an amount that avoids use of surfactants (such as Tween 80 or Cremophor), so that the composition is free or substantially free of surfactant (such as Tween 80 or Cremophor).

In some embodiments, the composition, in liquid form, comprises from about 0.1% to about 50% (w/v) (e.g. about 0.5% (w/v), about 5% (w/v), about 10% (w/v), about 15% (w/v), about 20% (w/v), about 30% (w/v), about 40% (w/v), about 50% (w/v)) of the carrier protein. In some embodiments, the composition, in liquid form, comprises about 0.5% to about 5% (w/v) of the carrier protein.

In some embodiments, the weight ratio of carrier protein, e.g., albumin, to the poorly water soluble pharmaceutical agent is such that a sufficient amount of poorly water soluble pharmaceutical agent binds to, or is transported by, the cell. While the weight ratio of carrier protein to pharmaceutical agent will have to be optimized for different carrier protein and drug combinations, generally the weight ratio of carrier protein, e.g., albumin, to pharmaceutical agent (w/w) is about 0.01:1 to about 100:1, including for example any of about 0.02:1 to about 50:1, about 0.05:1 to about 20:1, about 0.1:1 to about 20:1, about 1:1 to about 18:1, about 2:1 to about 15:1, about 3:1 to about 12:1, about 4:1 to about 10:1, about 5:1 to about 9:1, and about 9:1. In some embodiments, the carrier protein to pharmaceutical agent weight ratio is about any of 18:1 or less, such as about any of 15:1 or less, 14:1 or less, 13:1 or less, 12:1 or less, 11:1 or less, 10:1 or less, 9:1 or less, 8:1 or less, 7:1 or less, 6:1 or less, 5:1 or less, 4:1 or less, and 3:1 or less.

In some embodiments, the carrier protein allows the composition to be administered to an individual (such as human) without significant side effects. In some embodiments, the carrier protein (such as albumin) is in an amount that is effective to reduce one or more side effects of administration of the poorly water soluble pharmaceutical agent to a human. The term "reducing one or more side effects of administration of the poorly water soluble pharmaceutical agent" refers to reduction, alleviation, elimination, or avoidance of one or more undesirable effects caused by the poorly water soluble pharmaceutical agent, as well as side effects caused by delivery vehicles (such as solvents that render the poorly water soluble pharmaceutical agents suitable for injection) used to deliver the poorly water soluble pharmaceutical agent. Such side effects include, for example, myelosuppression, neurotoxicity, hypersensitivity, inflammation, venous irritation, phlebitis, pain, skin irritation, peripheral neuropathy, neutropenic fever, anaphylactic reaction, venous thrombosis, extravasation, and combinations thereof. These side effects, however, are merely exemplary and other side effects, or combination of side effects, associated with various pharmaceutical agents can be reduced.

In some embodiments, the composition comprises particles (such as nanoparticles) comprising (in various embodiments consisting of or consisting essentially of) a poorly water soluble pharmaceutical agent and an albumin, wherein the weight ratio of the albumin to the poorly water soluble pharmaceutical agent in the composition (w/w) is about 0.01:1 to about 100:1, including for example any of about 0.02:1 to about 50:1, about 0.05:1 to about 20:1, about 0.1:1 to about 20:1, about 1:1 to about 18:1, about 2:1 to about 15:1, about 3:1 to about 12:1, about 4:1 to about 10:1, about 5:1 to about 9:1, and about 9:1. In some embodiments, the carrier protein to pharmaceutical agent weight ratio is about any of 18:1 or less, 15:1 or less, 14:1 or less, 13:1 or less. 12:1 or less, 11:1 or less, 10:1 or less, 9:1 or less, 8:1 or less, 7:1 or less, 6:1 or less, 5:1 or less, 4:1 or less, and 3:1 or less. In some embodiments, the poorly water soluble pharmaceutical agent is coated with the albumin. In some embodiments, the particles (such as nanoparticles) comprising a poorly water soluble pharmaceutical agent and albumin are suspended in an aqueous medium (such as an aqueous medium containing albumin). For example, the composition can be a colloidal suspension of the poorly water soluble pharmaceutical agent particles (such as nanoparticles). In some embodiments, the composition is a dry (such as lyophilized) composition that can be reconstituted or resuspended to a stable suspension of particles or described herein. The concentration of the poorly water soluble pharmaceutical agent in the liquid composition or reconstituted composition can be dilute (0.1 mg/ml) or concentrated (100 mg/ml), including for example any of about 0.1 to about 50 mg/ml, about 0.1 to about 20 mg/ml, about 1 to about 10 mg/ml, about 2 mg/ml to about 8 mg/ml, about 4 to about 6 mg/ml, and 5 mg/ml. In some embodiments, the concentration of the poorly water soluble pharmaceutical agent (such as docetaxel) is greater than about 0.1 mg/ml. In some embodiments, the concentration of the poorly water soluble pharmaceutical agent is greater than about any of 1, 2, 3, 4, 5, 6, 7, 8, 9, 10, 11, 12, 13, 14, 15, 16, 17, 18, 19, 20, 25, 30, 35, 40, 45, or 50 mg/ml. In some embodiments, the poorly water soluble pharmaceutical agent is a taxane or a derivative thereof (such as docetaxel or a derivative thereof).

In some embodiments, the composition comprises particles (such as nanoparticles) comprising docetaxel, such as nanoparticles with an average or mean diameter of between about 20 to about 400 nm. In some embodiments, the particles have an average or mean diameter of between about 40 to about 200 nm. In some embodiments, the composition comprises particles (such as nanoparticles) comprising (in various embodiments consisting essentially of) docetaxel and albumin. In some embodiments, the docetaxel is coated with albumin. In some embodiments, the weight ratio of the albumin to the docetaxel (w/w) in the composition is about 0.01:1 to about 100:1, including for example any of about 0.02:1 to about 50:1, about 0.05:1 to about 20:1, about 1:1 to about 18:1, about 2:1 to about 15:1, about 3:1 to about 12:1. In some embodiments, the albumin to docetaxel ratio (w/w) is about any of 18:1 or less, 15:1 or less, 14:1 or less, 13:1 or less, 12:1 or less, 10:1 or less, 9:1 or less, 8:1 or less, 7:1 or less, 6:1 or less, 5:1 or less, 4:1 or less, and 3:1 or less.

In some embodiments, the particles (such as nanoparticles) comprising docetaxel and albumin are suspended in an aqueous medium (such as an aqueous medium containing the albumin). For example, the composition can be a colloidal suspension of the docetaxel-containing particles (such as nanoparticles). In some embodiments, the composition is a dry (such as lyophilized composition) that can be reconstituted to an aqueous suspension of the docetaxel-containing particles. In some embodiments, the concentration of the docetaxel in the composition is between about 0.1 mg/ml and about 100 mg/ml, including for example any of about 0.1 to about 50 mg/ml, about 0.1 to about 20 mg/ml, about 1 to about 10 mg/ml, about 2 to about 8 mg/ml, about 4 to about 6 mg/ml, and about 5 mg/ml. In some embodiments, the concentration of docetaxel is at least about any of 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, and 50 mg/ml.

Anhydrous Docetaxel

In addition to the use of stabilizing agents described herein (such as sodium citrate and sodium citrate/sodium chloride), it has been surprisingly found that the use of anhydrous docetaxel results in a more stable formulation than can be made with a hydrated docetaxel such as docetaxel trihydrate or hemi-hydrate. The anhydrous docetaxel formulations of the present invention further improve the stability of the aqueous nanoparticle suspensions such that stability of the suspensions, either before or after lyophilization, exceeds 1 day. In addition, the benefits of added stability of anhydrous docetaxel also extend to conventional formulations such as a formulation in Tween 80, Cremophor or other known surfactants.

Thus, in accordance with the present invention, docetaxel can be dissolved in pharmaceutically acceptable solvent or solvents at a final concentration in the range of about 1-99% v/v, more preferably in the range of about 5-25% v/v. Solvents include, for example, chlorinated solvents, ethyl acetate, ethanol, tetrahydrofuran, dioxane, acetonitrile, acetone, dimethyl sulfoxide, dimethyl formamide, methylpyrrolidinone, oils such as soybean oil, safflower oil and other injectable oils and the like.

In some embodiments, there is provided a composition comprising docetaxel, wherein the docetaxel used for preparation of the composition is in an anhydrous form. In some embodiments, the invention provides a composition comprising docetaxel, wherein at least some of the docetaxel in the composition is in an anhydrous form. For example, in some embodiments, at least about 10% (such as at least about any of 20%, 30%, 40%, and 50%) of the docetaxel in the composition is in an anhydrous form. In some embodiments, the composition further comprises a stabilizing agent (such as the stabilizing agent described herein).

In some embodiments, the composition comprises docetaxel and a biocompatible polymer (such as a carrier protein described herein, for example albumin), wherein the docetaxel used for preparation of the composition is in an anhydrous form. In some embodiments, the composition comprises docetaxel, a biocompatible polymer (such as a carrier protein described herein, for example albumin) and a stabilizing agent (such as a stabilizing agent described herein), wherein the docetaxel used for preparation of the composition is in an anhydrous form. In some embodiments, the composition is substantially free (such as free) of surfactants. In some embodiments, the composition comprises surfactant.

In some embodiments, the invention provides a composition comprising docetaxel and a biocompatible polymer (such as a carrier protein, for example albumin), wherein at least some of the docetaxel in the composition is in an anhydrous form. For example, in some embodiments, at least about 10% (such as at least about any of 20%, 30%, 40%, and 50%) of the docetaxel in the composition is in an anhydrous form. In some embodiments, the composition further comprises a stabilizing agent (such as the stabilizing agent described herein).

In some embodiments, the invention provides a composition comprising docetaxel and a surfactant (such as anhydrous surfactant), wherein the docetaxel used for preparation of the composition is in an anhydrous form. In some embodiments, the surfactant used for preparation of the composition is in an anhydrous form. Suitable surfactants include, for example, polysorbate (such as Tweens) and Cremophor. In some embodiments, the composition may further comprise a stabilizing agent described herein. In some embodiments, the invention provides a composition comprising docetaxel and a surfactant, wherein at least some of the docetaxel in the composition is in an anhydrous form. For example, in some embodiments, at least about 10% (such as at least about any of 20%, 30%, 40%, and 50%) of the docetaxel in the composition is in an anhydrous form.

In some embodiments, the composition described herein is a dry (such as lyophilized) composition that can be reconstituted, resuspended, or rehydrated generally to form a stable aqueous suspension of the docetaxel. In some embodiments, the composition is a liquid (such as aqueous) composition obtained by reconstituting or resuspending a dry composition. In some embodiments, the composition is an intermediate liquid (such as aqueous) composition that can be dried (such as lyophilized).

In some embodiments, there is provided a method of preparing compositions comprising docetaxel and a surfactant, wherein the method comprises combining an anhydrous docetaxel with the surfactant. In some embodiments, the surfactant used for preparation of the composition is anhydrous. In some embodiment, there is provided a method of preparing a composition comprising docetaxel and a biocompatible polymer (such as the carrier proteins, for example albumin), wherein the method comprises combining an anhydrous docetaxel with a biocompatible polymer (such as a carrier protein, for example albumin). Also provided are compositions produced by methods described herein.

Other Components in the Compositions

The compositions described herein can include other agents, excipients, or stabilizers to improve properties of the composition. Examples of suitable excipients and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. Examples of emulsifying agents include tocopherol esters such as tocopheryl polyethylene glycol succinate and the like, Pluronic®, emulsifiers based on polyoxy ethylene compounds, Span 80 and related compounds and other emulsifiers known in the art and approved for use in animals or human dosage forms. The compositions can be formulated so as to provide rapid, sustained or delayed release of the active ingredient after administration to the patient by employing procedures well known in the art.

Preferred compositions for administration by injection include those comprising a poorly water soluble pharmaceutical agent as the active ingredient in association with a surface-active agent (or wetting agent or surfactant), or in the form of an emulsion (e.g., as a water-in-oil or oil-in-water emulsion). Other ingredients can be added, for example, mannitol or other pharmaceutically acceptable vehicles, if necessary.

In some embodiments, the composition is suitable for administration to a human. In some embodiments, the composition is suitable for administration to a mammal such as, in the veterinary context, including domestic pets and agricultural animals. There are a wide variety of suitable formulations of the inventive composition (see, e.g., U.S. Pat. Nos. 5,916,596 and 6,096,331). The following formulations and methods are merely exemplary and are in no way limiting. Formulations suitable for oral administration can consist of (a) liquid solutions, such as an effective amount of the compound dissolved in diluents, such as water, saline, or orange juice, (b) capsules, sachets or tablets, each containing a predetermined amount of the active ingredient, as solids or granules, (c) suspensions in an appropriate liquid, (d) suitable emulsions, and (e) powders. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. Injectable formulations are preferred.

Formulations suitable for aerosol administration comprise the inventive composition include aqueous and non-aqueous, isotonic sterile solutions, which can contain anti-oxidants, buffers, bacteriostats, and solutes, as well as aqueous and non-aqueous sterile suspensions that can include suspending agents, solubilizers, thickening agents, stabilizers, and preservatives, alone or in combination with other suitable components, which can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressured preparations, such as in a nebulizer or an atomizer.

In some embodiments, the composition is formulated to have a pH in the range of about 4.5 to about 9.0, including for example pH in the ranges of any of about 5.0 to about 8.0, about 6.5 to about 7.5, and about 6.5 to about 7.0. In some embodiments, the pH of the composition is formulated to no less than about 6, including for example no less than about any of 6.5, 7, or 8 (such as about 7.5 or about 8). The composition can also be made to be isotonic with blood by the addition of a suitable tonicity modifier, such as glycerol.

Also provided are articles of manufacture comprising the compositions described herein in suitable packaging. Suitable packaging for compositions described herein are known in the art, and include, for example, vials (such as sealed vials), vessels (such as sealed vessels), ampules, bottles, jars, flexible packaging (e.g., sealed Mylar or plastic bags), and the like. These articles of manufacture may further be sterilized and/or sealed. Also provided are unit dosage forms comprising the compositions described herein. These unit dosage forms can be stored in a suitable packaging in single or multiple unit dosages and may also be further sterilized and sealed.

The present invention also provides kits comprising compositions (or unit dosages forms and/or articles of manufacture) described herein and may further comprise instruction(s) on methods of using the composition, such as uses further described herein. In some embodiments, the kit of the invention comprises the packaging described above. In other embodiments, the kit of the invention comprises the packaging described above and a second packaging comprising a buffer. It may further include other materials desirable from a commercial and user standpoint, including other buffers, diluents, filters, needles, syringes, and package inserts with instructions for performing any methods described herein.

Kits may also be provided that contain sufficient dosages of the poorly water soluble pharmaceutical agent (such as docetaxel) as disclosed herein to provide effective treatment for an individual for an extended period, such as any of a week, 2 weeks, 3 weeks, 4 weeks, 6 weeks, 8 weeks, 3 months, 4 months, 5 months, 6 months, 7 months, 8 months, 9 months or more. Kits may also include multiple unit doses of the poorly water soluble pharmaceutical agent and pharmaceutical compositions and instructions for use and packaged in quantities sufficient for storage and use in pharmacies, for example, hospital pharmacies and compounding pharmacies.

Method of Making and Using the Compositions

Also provided are methods of making and using compositions described herein. For example, there is provided a method of preparing a composition comprising a poorly water soluble pharmaceutical agent (such as a taxane, for example, paclitaxel, docetaxel, or ortataxel), optionally a biocompatible polymer (such as a carrier protein, for example albumin), and a stabilizing agent, wherein stability of the composition is enhanced as compared to that of a composition without the stabilizing agent, comprising combining (such as admixing) a composition containing a poorly water soluble pharmaceutical agent and optionally a biocompatible polymer (such as a carrier protein) with a stabilizing agent.

Also provided are methods for the formation of nanoparticles of docetaxel prepared under conditions of high shear forces (e.g., sonication, high pressure homogenization or the like). The preparation of nanoparticles from biocompatible polymers (e.g., albumin) is disclosed in, for example, U.S. Pat. Nos. 5,916,596; 6,506,405 and 6,537,579 and also in U.S. Patent Publication 2005/0004002 A1, incorporated herein by reference.

Briefly, the poorly water soluble pharmaceutical agent (such as docetaxel) is dissolved in an organic solvent, and the solution can be added to an aqueous albumin solution. The mixture is subjected to high pressure homogenization. The organic solvent can then be removed by evaporation. The dispersion obtained can be further lyophilized. Suitable organic solvents include, for example, ketones, esters, ethers, chlorinated solvents, and other solvents known in the art. For example, the organic solvent can be methylene chloride or chloroform/ethanol (for example with a ratio of 1:9, 1:8, 1:7, 1:6, 1:5, 1:4, 1:3, 1:2, 1:1, 2:1, 3:1, 4:1, 5:1, 6:1, 7:1, 8:1, or 9:1).

It was surprisingly found that compositions of docetaxel, such as those prepared in the above cited references, have stability lasting less than 1 day. In fact, when tested, many of the compositions were stable for only 4 to 8 hours. The present invention allows for increasing liquid stability and post-reconstitution stability by addition of certain stabilizers before the formation of nanoparticles or after the nanoparticles have formed.

There are therefore provided methods of stabilizing a composition comprising a poorly water soluble pharmaceutical agent, comprising combining the composition with a stabilizing agent, wherein the resultant composition is stable under the same condition under which the composition is unstable prior to the addition of the stabilizing agent. In some embodiments, the method further comprises identifying and selecting a composition that is unstable under certain conditions. In some embodiments, the composition for selection comprises a poorly water soluble pharmaceutical agent and a carrier protein (such as albumin). In some embodiments, the composition for selection comprises particles (such as nanoparticles) comprising the poorly water soluble pharmaceutical agent and a carrier protein (such as albumin).

Pharmaceutically acceptable excipients can also be added to the composition. The pharmaceutically acceptable excipients may be a solution, emulsion or suspension. For example, an emulsion of propofol in oil and stabilized by lecithin, is well known in the art. Other invention emulsion or nanoparticle formulations may also be prepared. An emulsion is formed by homogenization under high pressure and high shear forces. Such homogenization is conveniently carried out in a high-pressure homogenizer, typically operated at pressures in the range of about 3,000 up to 30,000 psi. Preferably, such processes are carried out at pressures in the range of about 6,000 up to 25,000 psi. The resulting emulsion comprises very small nanodroplets of the nonaqueous solvent containing the dissolved pharmacologically active agent and very small nanodroplets of the protein-stabilizing agent. Acceptable methods of homogenization include processes imparting high shear and cavitation such as, for example, high-pressure homogenization, high shear mixers, sonication, high shear impellers and the like.

Colloidal systems prepared in accordance with the present invention can be further converted into powder form by removal of the water, e.g., by lyophilization at a suitable temperature-time profile. The protein (e.g., HSA) itself acts as a cryoprotectant, and the powder is easily reconstituted by addition of water, saline or buffer, without the need to use conventional cryoprotectants such as mannitol, sucrose, glycine and the like. While not required, it is of course understood that conventional cryoprotectants can be added to the pharmaceutical compositions if so desired.

The stabilizing agent can either be admixed with the poorly water soluble pharmaceutical agent and/or the carrier protein during preparation of the poorly water soluble pharmaceutical agent/carrier protein composition, or added after the poorly water soluble pharmaceutical agent/carrier protein composition is prepared. For example, the stabilizing agent can be present in a protein solution prior to formation of the poorly water soluble pharmaceutical agent/carrier protein composition. The stabilizing agent may also be added along with an aqueous medium used to reconstitute/suspend the poorly water soluble pharmaceutical agent/carrier protein composition or added to an aqueous suspension of the carrier protein-associated poorly water soluble pharmaceutical agent. In some embodiments, the stabilizing agent is admixed with the poorly water soluble pharmaceutical agent/carrier protein composition prior to lyophilization. In some embodiments, the stabilizing agent is added as a dry component to the lyophilized pharmaceutical agent/carrier protein composition. In some embodiments when the composition comprises particles (such as nanoparticles), the stabilizing agent can be added either before or after the particles are formed.

In some embodiments when the addition of the stabilizing agent changes the pH of the composition, the pH in the composition are generally (but not necessarily) adjusted to a desired pH. Exemplary pH values of the compositions include, for example, about 5 to about 8.5. In some embodiments, the pH of the composition is adjusted to no less than about 6, including for example no less than about any of 6.5, 7, or 8 (such as about 7.5 or 8).

Also provided are methods of making pharmaceutical compositions comprising combining any of the compositions described herein (including those above) with a pharmaceutically acceptable excipient.

Also provided herein are methods of using the compositions of the present invention. In some embodiments, there is provided a method for treating a disease or condition that is responsive to a poorly water soluble pharmaceutical agent comprising administering a composition comprising an effective amount of a poorly water soluble pharmaceutical agent, optionally a biocompatible polymer (such as a carrier protein), and a stabilizing agent, wherein stability of the composition is enhanced as compared to that of a composition without the stabilizing agent. For example, in some embodiments, there is provided a method of treating cancer in an individual (such as human) comprising administering to the individual a composition comprising an effective amount of a poorly water soluble antineoplastic agent (such as docetaxel), optionally a carrier protein, and a stabilizing agent, wherein stability of the composition is enhanced as compared to that of a composition without the stabilizing agent. In some embodiments, the amount of the stabilizing agent in the composition does not cause any toxicological effects when the composition is administered into an individual (such as human). In some embodiments, the invention provides a method of treating cancer in an individual (such as human) comprising administering to the individual an effective amount of docetaxel, wherein the docetaxel used for preparation of the composition is in anhydrous form. For example, the docetaxel may be anhydrous prior to being incorporated into the composition.

The term "effective amount" used herein refers to an amount of a compound or composition sufficient to treat a specified disorder, condition or disease such as ameliorate, palliate, lessen, and/or delay one or more of its symptoms. In reference to cancers or other unwanted cell proliferation, an effective amount comprises an amount sufficient to cause a tumor to shrink and/or to decrease the growth rate of the tumor (such as to suppress tumor growth). In some embodiments, an effective amount is an amount sufficient to delay development. In some embodiments, an effective amount is an amount sufficient to prevent occurrence and/or recurrence. An effective amount can be administered in one or more administrations.

Cancers to be treated by compositions described herein (such as a composition comprising a poorly water soluble antineoplastic agent such as docetaxel, rapamycin, and 17-AAG) include, but are not limited to, carcinoma, lymphoma, blastoma, sarcoma, and leukemia. Examples of cancers that can be treated by compositions described herein include, but are not limited to, squamous cell cancer, lung cancer (including small cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, heptoma, breast cancer, colon cancer, melanoma, endometrical or uterine carcinoma, salivary gland carcinoma, kidney or renal cancer, liver cancer, prostate cancer, vulval cancer, thyroid cancer, hepatic carcinoma, head and neck cancer, colorectal cancer, rectal cancer, soft-tissue sarcoma, Kaposi's sarcoma, B-cell lymphoma (including low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, and Waldenstrom's macroglobulinemia), chronic lymphocytic leukemia (CLL), acute lymphoblastic leukemia (ALL), myeloma, Hairy cell leukemia, chronic myeloblastic leukemia, and post-transplant lymphoproliferative disorder (PTLD), as well as abnormal vascular proliferation associated with phakomatoses, edema (such as that associated with brain tumors), and Meigs' syndrome. In some embodiments, there is provided a method of treating metastatic cancer (that is, cancer that has metastasized from the primary tumor). In some embodiments, there is provided a method of reducing cell proliferation and/or cell migration. In some embodiments, there is provided a method of treating hyperplasia.

In some embodiments, there are provided methods of treating cancer at advanced stage(s). In some embodiments, there are provided methods of treating breast cancer (which may be HER2 positive or HER2 negative), including, for example, advanced breast cancer, stage IV breast cancer, locally advanced breast cancer, and metastatic breast cancer. In some embodiments, the cancer is lung cancer, including, for example, non-small cell lung cancer (NSCLC, such as advanced NSCLC), small cell lung cancer (SCLC, such as advanced SCLC), and advanced solid tumor malignancy in the lung. In some embodiments, the cancer is ovarian cancer, head and neck cancer, gastric malignancies, melanoma (including metastatic melanoma), colorectal cancer, pancreatic cancer, and solid tumors (such as advanced solid tumors). In some embodiments, the cancer is any of (and in some embodiments selected from the group consisting of) breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, gliomas, glioblastomas, neuroblastomas, and multiple myeloma. In some embodiments, the cancer is a solid tumor. In some embodiments, the cancer is any of (in some embodiments, selected from the group consisting of) prostate cancer, colon cancer, breast cancer, head and neck cancer, pancreatic cancer, lung cancer, and ovarian cancer.

Individuals suitable for receiving these compositions depend on the nature of the poorly water soluble pharmaceutical agent, as well as the disease/condition/disorder to be treated and/or prevented. Accordingly, the term individual includes any of vertebrates, mammals, and humans depending on intended suitable use. In some embodiments, the individual is a mammal. In some embodiments, the individual is any one or more of human, bovine, equine, feline, canine, rodent, or primate. In some embodiments, the individual is a human.

In another aspect, there is provided a method of treating carcinoma (such as colon carcinoma) in an individual, wherein the method comprises administering to the individual a composition comprising an effective amount of docetaxel and a carrier protein (such as albumin). In some embodiments, the composition further comprises a stabilizing agent described herein, such as citrate. In some embodiments, the docetaxel used for preparation of the composition that is administered to the individual is in an anhydrous form. The docetaxel and the carrier protein may be present in the forms of nanoparticles (such as nanoparticles described herein).

The compositions described herein can be administered alone or in combination with other pharmaceutical agents, including poorly water soluble pharmaceutical agents. For example, when the composition comprises a taxane (such as docetaxel), it can be co-administered with one or more other chemotherapeutic agents including, but are not limited to, carboplatin, Navelbine® (vinorelbine), anthracycline (Doxil), lapatinib (GW57016), Herceptin, gemcitabine (Gemzar®), capecitabine (Xeloda®), alimta, cisplatin, 5-fluorouracil, epirubicin, cyclophosphamide, avastin, Velcade®, etc. In some embodiments, the taxane composition is co-administered with a chemotherapeutic agent selected from the group consisting of antimetabolites (including nucleoside analogs), platinum-based agents, alkylating agents, tyrosine kinase inhibitors, anthracycline antibiotics, vinca alkloids, proteasome inhibitors, macrolides, and topoisomerase inhibitors. These other pharmaceutical agents can be present in the same composition as the drug (such as taxane), or in a separate composition that is administered simultaneously or sequentially with the drug (such as taxane)-containing composition. Combination therapy methods using nanoparticle formulations of taxane with other agents (or therapeutic methods) have been described in International Patent Application No. PCT/US2006/006167.

The dose of the inventive composition administered to an individual (such as human) will vary with the particular composition, the method of administration, and the particular disease being treated. The dose should be sufficient to effect a desirable response, such as a therapeutic or prophylactic response against a particular disease or condition. For example, the dosage of docetaxel administered can be about 1 to about 300 mg/m$^2$, including for example about 10 to about 300 mg/m$^2$, about 30 to about 200 mg/m$^2$, and about 70 to about 150 mg/m$^2$. Typically, the dosage of docetaxel in the composition can be in the range of about 50 to about 200 mg/m$^2$ when given on a 3 week schedule, or about 10 to about 100 mg/m$^2$ when given on a weekly schedule. In addition, if given in a metronomic regimen (e.g., daily or a few times per week), the dosage may be in the range of about 1-50 mg/m$^2$.

Dosing frequency for the composition includes, but is not limited to, at least about any of once every three weeks, once every two weeks, once a week, twice a week, three times a week, four times a week, five times a week, six times a week, or daily. In some embodiments, the interval between each administration is less than about a week, such as less than about any of 6, 5, 4, 3, 2, or 1 day. In some embodiments, the interval between each administration is constant. For example, the administration can be carried out daily, every two days, every three days, every four days, every five days, or weekly. In some embodiments, the administration can be carried out twice daily, three times daily, or more frequent.

The administration of the composition can be extended over an extended period of time, such as from about a month up to about three years. For example, the dosing regime can be extended over a period of any of about 2, 3, 4, 5, 6, 7, 8, 9, 10, 11, 12, 18, 24, 30, and 36 months. In some embodiments, there is no break in the dosing schedule. In some embodiments, the interval between each administration is no more than about a week.

The compositions described herein can be administered to an individual (such as human) via various routes, including, for example, intravenous, intra-arterial, intraperitoneal, intra-pulmonary, oral, inhalation, intravesicular, intramuscular, intra-tracheal, subcutaneous, intraocular, intrathecal, trans-mucosal, and transdermal. For example, the inventive composition can be administered by inhalation to treat conditions of the respiratory tract. The composition can be used to treat respiratory conditions such as pulmonary fibrosis, broncheolitis obliterans, lung cancer, bronchoalveolar carcinoma, and the like. In one embodiment of the invention, nanoparticles (such as albumin nanoparticles) of the inventive compounds can be administered by any acceptable route including, but not limited to, orally, intramuscularly, transdermally, intravenously, through an inhaler or other air borne delivery systems and the like.

When preparing the composition for injection, particularly for intravenous delivery, the continuous phase preferably comprises an aqueous solution of tonicity modifiers, buffered to a pH range of about 5 to about 8.5. The pH may also be below 7 or below 6. In some embodiments, the pH of the composition is no less than about 6, including for example no less than about any of 6.5, 7, or 8 (such as about 7.5 or 8).

The nanoparticles of this invention can be enclosed in a hard or soft capsule, can be compressed into tablets, or can be incorporated with beverages or food or otherwise incorporated into the diet. Capsules can be formulated by mixing the nanoparticles with an inert pharmaceutical diluent and inserting the mixture into a hard gelatin capsule of the appropriate size. If soft capsules are desired, a slurry of the nanoparticles with an acceptable vegetable oil, light petroleum or other inert oil can be encapsulated by machine into a gelatin capsule.

Also provided herein are methods of reducing side effects associated with administration of a poorly water soluble pharmaceutical agent to a human, comprising administering to a human a pharmaceutical composition comprising the poorly water soluble pharmaceutical agent, a biocompatible polymer (such as a carrier protein), and a stabilizing agent, wherein stability of the composition is enhanced as compared to that of a composition without the stabilizing agent. For example, the invention provides methods of reducing various side effects associated with administration of the poorly water soluble pharmaceutical agent, including, but not limited to, myelosuppression, neurotoxicity, hypersensitivity, inflammation, venous irritation, phlebitis, pain, skin irritation, peripheral neuropathy, neutropenic fever, anaphylactic reaction, hematologic toxicity, and cerebral or neurologic toxicity, and combinations thereof. In some embodiments, there is provided a method of reducing hypersensitivity reactions associated with administration of the poorly water soluble pharmaceutical agent, including, for example, severe skin rashes, hives, flushing, dyspnea, tachycardia, and others.

In addition, there is provided a method of enhancing stability of composition comprising a poorly water soluble pharmaceutical agent and optionally a biocompatible polymer (such as a carrier protein), comprising adding to the composition a stabilizing agent in an amount that is effective to enhance stability of the composition. In some embodiments, there is provided a method of preparing a composition comprising a poorly water soluble agent (such as docetaxel), a biocompatible polymer (such as a carrier protein, for example albumin), and a stabilizing agent, comprising combining (such as admixing) the poorly water soluble agent and the biocompatible polymer with the stabilizing agent. In some embodiments, the composition is a liquid composition. In some embodiments, the composition is a post-reconstitution composition.

The stabilizing agent can either be admixed with the poorly water soluble pharmaceutical agent and/or the carrier protein during preparation of the poorly water soluble pharmaceutical agent/carrier protein composition, or added along with an aqueous medium used to reconstitute the pharmaceutical/carrier protein composition.

In a further aspect of the invention is provided use of the compositions described herein in the manufacture of a medicament. Particularly, the manufacture of a medicament for use in the treatment of conditions described herein. Further, the pharmaceutical composition thereof, variously described herein, are also intended for use in the manufacture of a medicament for use in treatment of the conditions and, in accordance with the methods, described herein, unless otherwise noted.

Those skilled in the art will recognize that several variations are possible within the scope and spirit of this invention. The invention will now be described in greater detail by reference to the following non-limiting examples. Unless otherwise indicated, stabilities of the compositions in the examples below are evaluated either at 25° C. or 4° C.

Example 1

This example demonstrates the instability of a preparation of pharmaceutical compositions comprising docetaxel and albumin prepared as described in U.S. Patent Publication 2005/0004002 A1.

30 mg of docetaxel was dissolved in 2 mL chloroform/ethanol. The solution was then added into 27.0 mL of HSA solution (3% w/v). The mixture was homogenized for 5 minutes at low RPM (Vitris homogenizer model Tempest I.Q.) in order to form a crude emulsion, and then transferred into a high pressure homogenizer (Avestin). The emulsification was performed at 9000-40,000 psi. The resulting system was transferred into a Rotavap and solvent was rapidly removed at reduced pressure. The resulting dispersion was translucent and the typical average diameter of the resulting particles was in the range 50-220 nm (Z-average, Malvern Zetasizer). The dispersion was further lyophilized for 48 hours. The resulting cake was easily reconstituted to the original dispersion by addition of sterile water or saline. The particle size after reconstitution was the same as before lyophilization. When the liquid suspension prior to lyophilization was stored, it was surprisingly found that while the suspension was stable at about 4-8 hours after preparation, at 24 hours, there was some sedimentation indicating instability. Similarly, for the lyophilized reconstituted suspension it was surprisingly found that while the suspension was stable at about 4-8 hours after preparation, at 24 hours, there was some sedimentation indicating instability. This instability at 24 hours was not previously observed by the inventors as the monitoring period after initial formulation preparation and reconstitution was typically only 4-8 hours.

Example 2

This example demonstrates the instability of docetaxel nanoparticles prepared by sonication.

25.9 mg of docetaxel was added to a 20-mL scintillation vial and dissolved in 0.3 mL of chloroform. 4.7 mL of HSA (3.0%, w/v) was added to the docetaxel dissolved mixture. The composition was sonicated (Sonic Dismembrator, model 550, Fisher Scientific Company, Pittsburgh, Pa. 155275) is at 50% power for 1 min. The mixture was transferred into a rotary evaporator, and chloroform-ethanol was rapidly removed at 45° C., at reduced pressure. The diameter of the resulting docetaxel particles was 250-300 nm (Z-average, Malvern Zetasizer). The suspension precipitated in less than 1 day.

Example 3

This example demonstrates the instability of docetaxel nanoparticles prepared by sonication testing soybean oil as a stabilizer.

18.0 mg of docetaxel was added to a 20-mL scintillation vial and dissolved in 0.1 mL of chloroform-ethanol mixture. 0.05 mL of soybean oil and 2.35 mL of HSA (5.0%, w/v) was added to the above organic solvent. The sample was sonicated (Sonic Dismembrator, model 550, Fisher Scientific Company, Pittsburgh, Pa. 155275) for 2 min. The mixture is transferred into a rotary evaporator, and chloroform-ethanol is rapidly removed at 45° C., at reduced pressure. The diameter of the resulting docetaxel particles was ~270 nm (Z-average, Malvern Zetasizer). The suspension precipitated in less than 1 day.

Example 4

This example demonstrates the instability of docetaxel nanoparticles prepared by sonication using an ethyl acetate-n-butyl acetate mixture.

22.7 mg of docetaxel was added to a 20-mL scintillation vial and dissolved in 1.0 mL of ethyl acetate-n-butyl acetate mixture. 2.4 mL of HSA (5.0%, w/v) was added to the docetaxel dissolved in organic solvent. The sample was sonicated (Sonic Dismembrator, model 550, Fisher Scientific Company, Pittsburgh, Pa. 155275) at 50% power for 1 min. The mixture was transferred into a rotary evaporator, and ethyl acetate and n-butyl acetate are removed at reduced pressure. The composition precipitated within an hour.

Example 5

This example demonstrates the instability of docetaxel nanoparticles prepared by high pressure homogenization.

49.0 mg of docetaxel was dissolved in 0.56 mL of chloroform. The solution was added to 9.6 mL of HSA (5%, w/v). The mixture was pre-homogenized to form a crude emulsion, and then transferred into a high pressure homogenizer (Avestin). The emulsification was performed at 18,000-20,000 psi. The resulting system was transferred into a rotary evaporator, and chloroform and t-butyl alcohol were removed at reduced pressure. The diameter of the resulting docetaxel particles was 160-175 nm (Z-average, Malvern Zetasizer). Precipitation was observed in <1 day. Upon microscopic examination, the crystalline precipitates were seen.

Example 6

This example demonstrates the instability of docetaxel nanoparticles prepared by high pressure homogenization using lecithin.

55.3 mg of docetaxel and 48.8 mg of egg lecithin were dissolved in 0.56 mL of chloroform and t-butyl alcohol mixture. The solution was added to 9.6 mL of HSA (5%, w/v). The mixture was pre-homogenized to form a crude emulsion, and transferred into a high pressure homogenizer (Avestin). The emulsification was performed at 18,000-20,000 psi. The resulting system was transferred into a rotary evaporator, and chloroform and t-butyl alcohol were removed at reduced pressure. The diameter of the resulting docetaxel particles was 190-220 nm (Z-average, Malvern Zetasizer). Precipitation was observed in <24 hours.

Example 7

This example demonstrates the instability of docetaxel nanoparticles prepared by high pressure homogenization testing polylacticglycolic acid (PLGA).

56.3 mg of docetaxel and 40.8 mg of PLGA (50:50) were dissolved in 0.56 mL of chloroform. The solution was added to 9.6 mL of HSA (5%, w/v). The mixture was pre-homogenized to form a crude emulsion, and transferred into a high pressure homogenizer (Avestin). The emulsification was performed at 18,000-20,000 psi. The resulting system was transferred into a rotary evaporator, and chloroform and t-butyl alcohol were removed at reduced pressure. The diameter of the resulting docetaxel particles was 575 nm (Z-average, Malvern Zetasizer). Precipitation was observed in <24 hours.

Example 8

This example demonstrates the instability of docetaxel nanoparticles prepared by high pressure homogenization testing benzoic acid.

50.3 mg of docetaxel and 3.0 mg of benzoic acid were dissolved in 0.56 mL of chloroform and t-butyl alcohol mixture. The solution was added to 10.0 mL of HSA (5%, w/v). The mixture was pre-homogenized to form a crude emulsion, and transferred into a high pressure homogenizer (Avestin). The emulsification was performed at 18,000-20,000 psi. The resulting emulsion was transferred into a rotary evaporator, and chloroform and t-butyl alcohol were removed at reduced pressure. The diameter of the resulting docetaxel particles was 160 nm (Z-average, Malvern Zetasizer). The composition precipitated in <24 hours.

Example 9

This example demonstrates the instability of docetaxel nanoparticles prepared by high pressure homogenization testing cholesterol.

51.0 mg of docetaxel and 16.5 mg of cholesterol were dissolved in 0.56 mL of chloroform and t-butyl alcohol mixture. The solution was added to 10.0 mL of HSA (5%, w/v). The mixture was pre-homogenized to form a crude emulsion, and transferred into a high pressure homogenizer (Avestin). The emulsification was performed at 18,000-20,000 psi. The resulting emulsion was transferred into a rotary evaporator, and chloroform and t-butyl alcohol were removed at reduced pressure. Precipitation occurred in <24 hours.

Example 10

This example demonstrates the stability of docetaxel nanoparticles prepared by high pressure homogenization testing sodium citrate.

50.0 mg of docetaxel was dissolved in 0.56 mL of chloroform and t-butyl alcohol mixture (10.2:1 (v/v)). The solution was added to 9.6 mL of HSA (5%, w/v) containing 100 mM (2.94% w/v) trisodium citrate. The mixture was pre-homogenized to form a crude emulsion, and transferred into a high pressure homogenizer (Avestin). The emulsification was performed at 18,000-20,000 psi. The resulting emulsion was transferred into a rotary evaporator, and chloroform and t-butyl alcohol was removed at reduced pressure. The diameter of the resulting docetaxel particles were 150-225 nm (Z-average, Malvern Zetasizer). The formulation was surprisingly stable >24 hours without observable precipitate.

Example 11

This example demonstrates the stability of docetaxel nanoparticle preparation with citrate (3.9%, 133 mM) and sodium chloride (1.75%, 300 mM).

The aqueous phase were prepared by adding HSA (5% by weight), sodium citrate (3.9% by weight) and sodium chloride (1.75% by weight) into water for injection and stirred until dissolved. The organic phase was prepared by dissolving docetaxel (7% by weight) into a solvent mixture (6% by volume) containing chloroform and ethanol and stirred until dissolved. Slowly, the organic phase was added to the aqueous phase and mixed with a rotorstator mixer. The batch size was 20 ml. The crude emulsion was high pressure homogenized at 20,000 psi. The chloroform and ethanol in the emulsion was then removed using a rotary evaporator at a reduced pressure. The suspension was filtered by serial filtration (1.2 μm, 0.8 μm, and 0.45 μm) and then lyophilized (FTS Tray Freeze Dryer).

The liquid suspension is homogeneous and off-white. Particle size analysis was performed using a Malvern Zetasizer. The particles had an average size of 165.6 nm. The sample was also examined by microscopy and most of the particles were <0.5 μm. The suspension was stored at both 4° C. and 25° C. Surprisingly, the suspension was stable up to 3 days at 4° C. and >1 day at 25° C. The suspension did not exhibit any settling or precipitation, and didn't change color or consistency. Furthermore, the lyophilized product appeared as a solid cake. The reconstitution of the lyophilized cake took <5 min. After reconstitution, the particles had an average particle size of 164.6 nm. The reconstituted suspension was stored at 4° C. and surprisingly remained stable >1 day.

Example 12

This example demonstrates the stability of docetaxel nanoparticle preparation with citrate (2.9%, 100 mM) and sodium chloride (1.75%, 300 mM).

The aqueous phase was prepared by adding HSA (5% by weight), sodium citrate (2.9% by weight) and sodium chloride (1.75% by weight) into water for injection and stirred until dissolved. The organic phase was prepared by dissolving docetaxel (7% by weight) into a solvent mixture (6% by volume) containing chloroform and ethanol and stirred until dissolved. The organic phase was added to the aqueous phase and mixed using a rotorstator mixer. The crude emulsion was high pressure homogenized at 20,000 psi. The chloroform and ethanol in the emulsion were removed using a rotary evaporator at reduced pressure. The suspension was filtered by serial filtration (1.2 μm, 0.8 μm, and 0.45 μm) and lyophilized (FTS Tray Freeze Dryer).

The liquid suspension was homogeneous and off-white. Particle size analysis was performed using a Malvern Zetasizer. The particles had an average size of 157.1 nm. The sample was also examined by microscopy and most of the particles were <0.5 μm. The suspension was stored at both 4° C. and 25° C. Surprisingly, the suspension was stable up to 3 days at 4° C. and >1 day at 25° C. The suspension didn't exhibit any settling or creaming, and didn't change color or consistency.

The lyophilized product appeared as a solid cake. The reconstitution of the lyophilized cake took <5 min. After reconstitution, the particles had an average particle size of 150.9 nm. The reconstituted suspension was stored at 4° C. and remained stable >1 day.

Example 13

This example demonstrates the stability of docetaxel nanoparticle preparation with citrate (3.9%, 133 mM).

The aqueous phase was prepared by adding HSA (5% by weight) and sodium citrate (3.9% by weight) into water for injection and stirred until dissolved. The organic phase was prepared by dissolving docetaxel (5% by weight) into a solvent mixture (6% by volume) containing chloroform and ethanol and stirred until dissolved. Slowly, the organic phase was added to the aqueous phase and mixed using a rotorstator mixer. The batch size was 20 ml. The crude emulsion was high pressure homogenized at 20,000 psi. The chloroform and ethanol in the emulsion were removed using a rotary evaporator at reduced pressure. The suspension was filtered by serial filtration (1.2 μm, 0.8 μm, 0.45 μm and 0.22 μm) and then lyophilized (FTS Tray Freeze Dryer).

The liquid suspension was homogeneous and off-white. Particle size analysis was performed using a Malvern Zetasizer. The particles had an average size of 131 nm. The sample was also examined by microscopy and most of the particles were <0.5 μm. Surprisingly the nanoparticle suspension was stable for >1 day.

Example 14

This example demonstrates the stability of docetaxel nanoparticle preparation with citrate (11.7%, 400 mM).

The aqueous phase was prepared by adding HSA (5% by weight) and sodium citrate (11.7% by weight) and into water for injection and stirred until dissolved. The organic phase was prepared by dissolving docetaxel (5% by weight) into a solvent mixture (6% by volume) containing chloroform and ethanol and stirred until dissolved. Slowly, the organic phase was added to the aqueous phase and mixed using a rotorstator mixer. The batch size was 20 ml. The crude emulsion was high pressure homogenized at 20,000 psi. The chloroform and ethanol in the emulsion were then removed using a rotary evaporator at a reduced pressure. The suspension was filtered by serial filtration (1.2 μm, 0.8 μm, 0.45 μm and 0.22 μm) and then lyophilized (FTS Tray Freeze Dryer).

The liquid suspension was homogeneous and off-white. Particle size analysis was performed using a Malvern Zetasizer. The particles had an average size of 143.5 nm. The sample was also examined by microscopy and most of the particles were <0.5 μm. The suspension was stored at both 4° C. and 25° C. Surprisingly, the suspension was stable up to 3 days at 4° C. and >1 day at 25° C. The suspension didn't exhibit any settling or creaming, and didn't change color or consistency.

The lyophilized product appeared as a solid cake. The reconstitution of the lyophilized cake took <5 min. After reconstitution, the particles had an average particle size of 151.8 nm. Surprisingly, the reconstituted suspension was stored at 4° C. and remained stable >1 day.

Example 15

This example demonstrates the stability of docetaxel nanoparticle preparation with citrate (7.7%, 200 mM).

The aqueous phase was prepared by adding HSA (5% by weight) and sodium citrate (7.7% by weight) and into water for injection and stirred until dissolved. The organic phase was prepared by dissolving docetaxel (5% by weight) into a solvent mixture (6% by volume) containing chloroform and ethanol and stirred until dissolved. Slowly, the organic phase was added to the aqueous phase and mixed using a rotorstator mixer. The batch size was 20 ml. The crude emulsion was high pressure homogenized at 20,000 psi. The chloroform and ethanol in the emulsion were removed using a rotary evaporator at reduced pressure. The suspension was filtered by serial filtration (1.2 μm, 0.8 μm, 0.45 μm and 0.22 μm) and then lyophilized (FTS Tray Freeze Dryer).

The liquid suspension is homogeneous and off-white. Particle size analysis was performed using a Malvern Zetasizer. The particles have an average size of 226.4 nm. The sample was also examined by microscopy and most of the particles were <0.5 μm. The suspension was stored at both 4° C. and 25° C. Surprisingly, the suspension was stable up to 3 days at 4° C. and >1 day at 25° C. The suspension didn't exhibit any settling or creaming, and didn't change color or consistency.

The lyophilized product appeared as a solid cake. The reconstitution of the lyophilized cake took <5 min. After reconstitution, the particles had an average particle size of 211.4 nm. The reconstituted suspension was stored at 4° C. and remained stable >1 day.

Example 16

This example demonstrates the stability of docetaxel nanoparticle preparation with citrate/NaCl.

The aqueous phase was prepared by adding HSA (5% by weight) and sodium citrate (5.88%, 200 mM) and NaCl (1.75%, 300 mM) and into water for injection and stirred until dissolved. The organic phase was prepared by dissolving docetaxel (5% by weight) into a solvent mixture (6% by volume) containing chloroform and ethanol and stirred until dissolved. Slowly, the organic phase was added to the aqueous phase and mixed using a rotorstator mixer. The batch size was 20 ml. The crude emulsion was high pressure homogenized at 20,000 psi. The solvents in the emulsion were removed using a rotary evaporator at reduced pressure. The suspension was filtered by serial filtration and then lyophilized (FTS Tray Freeze Dryer).

The liquid suspension was homogeneous and off-white. Particle size analysis was performed using a Malvern Zetasizer. The particles had an average size of <200 nm. The sample was also examined by microscopy and most of the particles were <0.5 µm. The suspension was stored and surprisingly, the suspension was stable without precipitates or sediment for >1 day.

The lyophilized product appeared as a solid cake. The reconstitution of the lyophilized cake took <5 min. The reconstituted suspension was stored and surprisingly remained stable >1 day.

Example 17

This example demonstrates the stability of a docetaxel nanoparticle preparation with citrate/NaCl.

The aqueous phase was prepared by adding HSA (5% by weight) and sodium citrate (2.94%, 100 mM) and NaCl (2.9%, 500 mM) and into water for injection and stirred until dissolved. The organic phase was prepared by dissolving docetaxel (5% by weight) into a solvent mixture (6% by volume) containing chloroform and ethanol and stirred until dissolved. Slowly, the organic phase was added to the aqueous phase and mixed using a rotorstator mixer. The batch size was 20 ml. The crude emulsion was high pressure homogenized at 20,000 psi. The solvents in the emulsion were removed using a rotary evaporator at reduced pressure. The suspension was filtered by serial filtration and then lyophilized (FTS Tray Freeze Dryer).

The liquid suspension was homogeneous and off-white. Particle size analysis was performed using a Malvern Zetasizer. The particles had an average size of <200 nm. The sample was also examined by microscopy and most of the particles were <0.5 µm. The suspension was stored and surprisingly, the suspension was stable without precipitates or sediment for >1 day.

The lyophilized product appeared as a solid cake. The reconstitution of the lyophilized cake took <5 min. The reconstituted suspension was stored and surprisingly remained stable >1 day.

Example 18

This example demonstrates the stability of a docetaxel nanoparticle preparation with citrate/NaCl.

The aqueous phase was prepared by adding HSA (5% by weight) and sodium citrate (2.94%, 100 mM) and NaCl (3.5%, 600 mM) and into water for injection and stirred until dissolved. The organic phase was prepared by dissolving docetaxel (5% by weight) into a solvent mixture (6% by volume) containing chloroform and ethanol and stirred until dissolved. Slowly, the organic phase was added to the aqueous phase and mixed using a rotorstator mixer. The batch size was 20 ml. The crude emulsion was high pressure homogenized at 20,000 psi. The solvents in the emulsion were removed using a rotary evaporator at reduced pressure. The suspension was filtered by serial filtration and then lyophilized (FTS Tray Freeze Dryer).

The liquid suspension was homogeneous and off-white. Particle size analysis was performed using a Malvern Zetasizer. The particles had an average size of <200 nm. The sample was also examined by microscopy and most of the particles were <0.5 µm. The suspension was stored and surprisingly, the suspension was stable without precipitates or sediment for >1 day.

The lyophilized product appeared as a solid cake. The reconstitution of the lyophilized cake took <5 min. The reconstituted suspension was stored and surprisingly remained stable >1 day.

Example 19

This example demonstrates the stability of a docetaxel nanoparticle preparation with citrate/NaCl.

The aqueous phase was prepared by adding HSA (5% by weight) and sodium citrate (1.47%, 50 mM) and NaCl (2.9%, 500 mM) and into water for injection and stirred until dissolved. The organic phase was prepared by dissolving docetaxel (5% by weight) into a solvent mixture (6% by volume) containing chloroform and ethanol and stirred until dissolved. Slowly, the organic phase was added to the aqueous phase and mixed using a rotorstator mixer. The batch size was 20 ml. The crude emulsion was high pressure homogenized at 20,000 psi. The solvents in the emulsion were removed using a rotary evaporator at reduced pressure. The suspension was filtered by serial filtration and then lyophilized (FTS Tray Freeze Dryer).

The liquid suspension was homogeneous and off-white. Particle size analysis was performed using a Malvern Zetasizer. The particles had an average size of <200 nm. The sample was also examined by microscopy and most of the particles were <0.5 µm. The suspension was stored and surprisingly, the suspension was stable without precipitates or sediment for >1 day.

The lyophilized product appeared as a solid cake. The reconstitution of the lyophilized cake took <5 min. The reconstituted suspension was stored and surprisingly remained stable >1 day.

Example 20

This example demonstrates the effect of anhydrous vs hydrated docetaxel nanoparticle preparation with citrate/NaCl.

The aqueous phase was prepared by adding HSA (5% by weight) and sodium citrate (200 mM) and NaCl (300 mM) and into water for injection and stirred until dissolved. The organic phase for three different formulations were prepared by dissolving either anhydrous docetaxel, docetaxel trihydrate or docetaxel hemi-hydrate (partial hydrate) (5% by weight) into a solvent mixture (6% by volume) containing chloroform and ethanol and stirred until dissolved. Slowly, the organic phase was added to the aqueous phase and mixed using a rotorstator mixer. The crude emulsion was high pressure homogenized at 20,000 psi. The solvents in the emulsion were removed using a rotary evaporator at reduced pressure. The suspension was filtered by serial filtration and then lyophilized (FTS Tray Freeze Dryer).

The liquid suspension was homogeneous and off-white. Particle size analysis was performed using a Malvern Zetasizer. The particles have an average size of <200 nm. The three suspensions were stored and surprisingly, the suspension containing the anhydrous docetaxel was the most stable without precipitates or sediment for >1 day. Both the hydrated docetaxel preparations showed precipitate or sediment in <1 day. The same observation was seen for the lyophilized suspension upon reconstitution. Thus it was determined that the anhydrous form of docetaxel was most suitable for a nanoparticle docetaxel preparation.

Example 20A

This example provides a comparison of anhydrous docetaxel, docetaxel trihydrate and docetaxel hemihydrate by Differential Scanning Calorimetry (DSC).

The three different types of docetaxel were subject to DSC using standard techniques. All showed a melting endotherm at about 162-166° C. However only the 2 hydrated materials showed a water dehydration endotherm between about 74-80° C.

Example 20B

This example provides a comparison of anhydrous docetaxel, docetaxel trihydrate and docetaxel hemihydrate by X-Ray Powder Diffraction (XRD).

The three different types of docetaxel were subject to XRD using standard techniques. The three materials all showed a variety of sharp peaks indicating crystallinity. However, the anhydrous material showed a different spectrum as compared to the two hydrated materials. In particular was a peak occurring at 2-theta of 7-8 for the anhydrous sample which was absent from the hydrated material. This indicated a different crystal structure for the anhydrous docetaxel versus the hydrated docetaxels.

Example 21

This example demonstrates that the degree of hydration affects the solubility of docetaxel and provides a comparison of the solubility of anhydrous docetaxel, docetaxel trihydrate and docetaxel hemihydrate.

To compare if the different types of docetaxel material had different solubility profiles as a result of their different structures, their solubility rates were compared in the solvent acetonitrile. Acetonitrile was added to a fixed amount of docetaxel from different suppliers to obtain a concentration of 5 mg/mL (anhydrous basis). The rate at which dissolution of the different docetaxels occurred was observed. It was observed that the anhydrous docetaxels (from 2 different suppliers) dissolved completely in less than 1 minute. In contrast the hydrated materials (trihydrate and partial hydrate from 2 different suppliers) did not readily dissolve and additional solvent had to be added to a final concentration of 2.5 mg/mL. Under these further diluted conditions, the time to dissolve was between 5 and 10 minutes for the hydrated materials. A similar observation was made when using the solvent chloroform. Thus, it is surprisingly found that the degree of hydration or anhydrous nature can substantially affect the solubility of docetaxel.

Example 22

This example demonstrates that the degree of hydration of docetaxel affects the stability and provides a comparison of the formulations of docetaxel trihydrate, hemihydrate and anhydrous docetaxel in Tween 80.

It is well known that docetaxel is formulated with Tween 80 as a solubilizer or emulsifier for the commercial product Taxotere. The different docetaxels were dissolved in Tween 80 at a concentration of 40 mg/mL (on anhydrous basis). 2 mL of these solutions were observed for stability over time. It was surprisingly found that after a few days, a sediment or precipitate was observed for the hydrated docetaxel but no precipitate was observed with the anhydrous docetaxel. Thus, the anhydrous docetaxel is preferred in the Tween formulation. In addition it may be useful to use a Tween 80 or equivalent surfactant that is anhydrous or very low in water content as the anhydrous form of docetaxel may absorb water to form the hydrated form which could result in precipitation.

Example 23

This example demonstrates the stability of a docetaxel nanoparticle preparation with anhydrous docetaxel and without added stabilizers.

The aqueous phase was prepared by adding HSA (5% by weight) to water for injection. The organic phase was prepared by dissolving anhydrous docetaxel (5% by weight) into a solvent mixture (6% by volume) containing chloroform and ethanol and stirred until dissolved. Slowly, the organic phase was added to the aqueous phase and mixed using a rotorstator mixer. The crude emulsion was high pressure homogenized at 20,000 psi. The solvents in the emulsion were removed using a rotary evaporator at reduced pressure. The suspension was filtered by serial filtration and then lyophilized (FTS Tray Freeze Dryer).

The liquid suspension was homogeneous and off-white. Particle size analysis was performed using a Malvern Zetasizer. The particles had an average size of <200 nm. The sample was also examined by microscopy and most of the particles were <0.5 μm. The suspension was stored and surprisingly, the suspension was stable without precipitates or sediment for approximately 1 day. Thus, in the absence of stabilizers Nab-docetaxel prepared with anhydrous docetaxel appears to be more stable than when prepared with a hydrated form of docetaxel for which stability is much less than 1 day, typically only a few hours.

Example 24

This example demonstrates the preparation of anhydrous docetaxel nanoparticle preparation with citrate/NaCl.

The aqueous phase was prepared by adding HSA (8.5% by weight) and sodium citrate (200 mM) and NaCl (300 mM) and into water for injection and stirred until dissolved. The organic was prepared by dissolving anhydrous docetaxel (133 mg/ml) into a solvent mixture containing chloroform and ethanol (1:1) and stirring until dissolved. Slowly, the organic phase (6% by volume) was added to the aqueous phase and mixed using a rotorstator mixer. The batch size was 200 ml. The crude emulsion was high pressure homogenized at 20,000 psi. The solvents in the emulsion were removed using a rotary evaporator at reduced pressure. The suspension was filtered by serial filtration and then lyophilized (FTS Tray Freeze Dryer).

The liquid suspension was homogeneous and off-white. Particle size analysis was performed using a Malvern Zetasizer. The particles had an average size of <200 nm. The suspension was stored and surprisingly, showed no precipitates or sediment for >1 day. The same observation was seen for the lyophilized suspension upon reconstitution.

Example 25

This example demonstrates the preparation of anhydrous docetaxel nanoparticle preparation with citrate/NaCl.

The aqueous phase was prepared by adding HSA (5% by weight) and sodium citrate (200 mM) and NaCl (300 mM) and into water for injection and stirred until dissolved. The organic phase was prepared by dissolving anhydrous docetaxel (160 mg/ml) into a solvent mixture containing chloroform and ethanol (1:1) and stirring until dissolved. Slowly, the organic phase (8% by volume) was added to the aqueous phase and mixed using a rotorstator mixer. The batch size was 200 ml. The crude emilsion was subject to high pressure homogenization at 20,000 psi. The solvents in the emulsion was removed using a rotary evaporator at reduced pressure. The suspension was filtered by serial filtration and then lyophilized (FTS Tray Freeze Dryer).

The liquid suspension was homogeneous and off-white. Particle size analysis was performed using a Malvern Zetasizer. The particles had an average size of less than 200 nm. The suspension was stored and, surprisingly, showed no precipitation or sedimentation for more than one day. The same observation was seen for the lyophilized suspension upon reconstitution.

Example 26

This example demonstrates the preparation of anhydrous docetaxel nanoparticle preparation with citrate/NaCl.

The aqueous phase was prepared by adding HSA (5% by weight) and sodium citrate (200 mM) and NaCl (300 mM) and into water for injection and stirred until dissolved. The organic phase was prepared by dissolving anhydrous docetaxel (160 mg/ml) into a solvent mixture containing chloroform and ethanol (1:1) and stirring until dissolved. Slowly, the organic phase (8% by volume) was added to the aqueous phase and mixed using a rotorstator mixture. The batch size was 200 ml. The crude emulsion was subject to high pressure homogenization at 20,000 psi. The solvents in the emulsion were removed using a rotary evaporator at reduced pressure. Additional albumin was added to the evaporated suspension to increase the albumin: drug ratio to 8:1 by weight. The suspension was filtered by serial filtration and then lyophilized (FTS Tray Freeze Dryer).

The liquid suspension was homogeneous and off-white. Particle size analysis was performed using a Malvern Zetasizer. The particles had an average size of less than 200 nm. The suspension was stored and, surprisingly, showed no precipitates or sediment for more than one day. The same observation was seen for lyophilized suspension upon reconstitution.

Example 27

This example demonstrates effect of pH on stability of the nanoparticle suspension as well as on chemical degradation of docetaxel.

Formulations of nanoparticle docetaxel were prepared as described in the above examples. The effect of pH on these formulations was tested between pH 4 and pH 9. Increasing pH above pH 6 was found to increase physical stability measured in terms of nanoparticle size and sedimentation of the formulation while at the same time increasing the amount of degradation of docetaxel to 7-epi docetaxel at room temperature. An optimal pH range in which both the physical stability and chemical stability was acceptable was thus found to be between 6-8.5. A more preferable pH range was 6.5-8 and a most preferable range was found to be pH 7.25 to 7.75.

Example 28

This example compares the stability of Nab-docetaxel prepared with either hydrated forms of docetaxel or anhydrous docetaxel in the presence or absence of suitable stabilizers.

Stability of these preparations was examined visually prior to lyophilization and well as upon reconstitution of the lyophilized preparations. In addition, the stability of lyophilized preparations (containing stabilizers) upon reconstitution was evaluated at different concentration of docetaxel in the reconstituted suspension. The results are set forth in Tables 1-3 below.

TABLE 1

Stability evaluation of Nab-docetaxel nanoparticle suspension prior to lyophilization

| State of Hydration of Docetaxel | Stability Observations Nab-docetaxel with no stabilizers | Stability Observations Nab-docetaxel with stabilizer (Citrate 200 mM/NaCl 300 mM) |
| --- | --- | --- |
| Hemihydrate (Batch I) | Immediate sedimentation (<15 min) of nanoparticle suspension once formed | Data not obtained |
| Trihydrate (Batch I) | Sedimentation of nanoparticle suspension in approximately 1 hour | Sedimentation of nanoparticle suspension by day 1 at 4° C. |
| Anhydrous (Batch I) | Sedimentation of nanoparticle filtrate by day 1 at 4° C. | No sedimentation of nanoparticle filtrate for 2 days at 4° C. |
| Anhydrous (Batch II) | Sedimentation of nanoparticle filtrate by day 1 at 4° C. | No sedimentation of nanoparticle filtrate for 2 days at 4° C. |

As shown in Table 1, stability of Nab-docetaxel prepared using anhydrous docetaxel was significantly better than Nab-docetaxel prepared using hydrated forms of docetaxel whether or not stabilizers were present in the formulation.

Addition of stabilizers (200 mM citrate/300 mM NaCl) significantly improved stability of Nab-docetaxel preparations containing no stabilizer.

Addition of stabilizers improved stability of Nab-docetaxel preparations made from docetaxel trihydrate.

TABLE 2

Reconstitution stability of Nab-docetaxel lyophilized powder containing stabilizer (citrate 200 mM/NaCl 300 mM) reconstituted to 5 mg/mL docetaxel in water for injection

| Docetaxel type: Trihydrate/Anhydrous | 15 min | 1 hr | 2 hr | 4 hr | 6 hr | 24 hr |
|---|---|---|---|---|---|---|
| Trihydrate (25° C.) | 1 | 2 | 2 | 3 | 4 | 4 |
| Anhydrous (25° C.) | 1 | 1 | 1 | 1 | 1 | 1 |
| Trihydrate (40° C.) | 1 | 2 | 4 | 4 | 4 | 4 |
| Anhydrous (40° C.) | 1 | 1 | 1 | 1 | 1 | 1 |

Code:
1 - No sedimentation
2 - Slight sedimentation
3 - More sedimentation
4 - Thick sedimentation
5 - Complete sedimentation

TABLE 3

Reconstitution stability of Nab-docetaxel lyophilized powder containing stabilizer (citrate 200 mM/NaCl 300 mM) reconstituted to 1 mg/mL docetaxel in water for injection

| Trihydrate/Anhydrous | 15 min | 1 hr | 2 hr | 4 hr | 6 hr | 24 hr |
|---|---|---|---|---|---|---|
| Trihydrate (4° C.) | 2 | 3 | 5 | 5 | 5 | 5 |
| Anhydrous (4° C.) | 1 | 3 | 5 | 5 | 5 | 5 |
| Trihydrate (25° C.) | 2 | 3 | 5 | 5 | 5 | 5 |
| Anhydrous (25° C.) | 1 | 3 | 5 | 5 | 5 | 5 |
| Trihydrate (40° C.) | 3 | 3 | 5 | 5 | 5 | 5 |
| Anhydrous (40° C.) | 2 | 3 | 5 | 5 | 5 | 5 |

Code:
1 - No sedimentation
2 - Slight sedimentation
3 - More sedimentation
4 - Thick sedimentation
5 - Complete sedimentation As shown in Tables 2 and 3, stability of reconstituted Nab-docetaxel containing stabilizers is significantly improved at a higher concentration of 5 mg/ml docetaxel versus a lower concentration of about 1 mg/ml docetaxel. Stability of the reconstituted Nab-docetaxel formulation containing stabilizers prepared with anhydrous docetaxel is significantly better than Nab-docetaxel prepared with docetaxel trihydrate.

Example 29

This example demonstrates the toxicity profiles of nanoparticle albumin formulation of docetaxel (Nab-docetaxel) vs Taxotere.

Maxiumum tolerated dose (MTD) for Nab-docetaxel and Taxotere® (Tween 80-docetaxel) were determined during a dose escalation study in nude mice. Nude mice, group size of 10 per group, were treated with increasing dose of Taxotere (0 mg/kg, 7 mg/kg, 15 mg/kg, 22 mg/kg, 33 mg/kg, and 50 mg/kg) using a q4dx3 schedule. Nude mice, group size of 6 per group, were treated with increasing dose of Nab-docetaxel (0 mg/kg, 15 mg/kg, 22 mg/kg, 33 mg/kg, 50 mg/kg, and 75 mg/kg) using a q4dx3 schedule. Animals were weighed every other day. Maximum body weight loss was plotted versus dose and fitted using a Hill equation. MTD defined as weight loss equal to 20% was calculated using the fitted data. The MTD was 2.3 fold higher for Nab-docetaxel versus Taxotere (Tween 80 docetaxel). MTDs were 47.2 mg/kg and 20.6 mg/kg for Nab-docetaxel and Taxotere, respectively.

Example 30

This example demonstrates the antitumor efficacy of invention nanoparticle docetaxel (Nab-docetaxel) with stabilizer vs Taxotere.

Efficacy of Nab-docetaxel (prepared with 200 mM citrate and 300 mM NaCl) was compared against Taxotere in a xenograft tumor model in nude mice bearing human HCT-116 colon tumor. 10 mice per group were used for the study. Taxotere was dosed at 15 mg/kg and Nab-docetaxel was dosed at 22 mg/kg, both on a q4dx3 schedule. Nab-docetaxel (22 mg/kg) was more effective in tumor suppression than Taxotere (15 mg/kg, MTD) with $p<0.0001$. In addition, Nab-Docetaxel exhibited greater therapeutic index than Taxotere as maximum weight loss in the Taxotere group was 20%, while that for Nab-docetaxel was about 17%, despite a 50% higher dose.

Example 31

This example demonstrates an infusion study of Nab-docetaxel (200 mM citrate/300 mM NaCl).

A study in rats was conducted with 5 min infusion of Nab-docetaxel, with increasing infusion rates of Nab-docetaxel formulation containing approx 200 mM of citrate/300 mM NaCl. A 5 min infusion in rats may be considered equivalent to 30 min infusion in humans.

Maximum safe infusion rate was ~0.5 ml/min. This is equivalent to 0.23 mmol/kg/min or 68 mg/kg/min of citrate for 5 min infusion in rats. Translated to human dose, this was equivalent to approximately 170 mg docetaxel/$m^2$ in a 30 min infusion.

Example 32

This example demonstrates the blood biocompatibility of 5 mg/ml Nab-docetaxel (200 mM citrate/300 mM NaCl).

An in vitro hemolysis study in rat blood was conducted using a placebo formulation (all components except docetaxel) and the Nab-docetaxel formulation. The placebo did not cause hemolysis even at the highest rat blood:placebo ratio of 1:1. The Nab-docetaxel formulation interfered with the absorption reading due to the characteristic light-scattering by nanoparticles, but when appropriate background/controls were performed, no hemolysis was detected at the highest rat blood:Nab-docetaxel ratio of 1:1. This demonstrates that Nab-docetaxel with stabilizer as indicated is compatible with rat blood.

Example 33

This example provides a pilot multiple dose escalation study in rats. All Nab-docetaxel formulations described herein contain 200 mM citrate and 300 mM NaCl.

To compare the safety of the Nab-docetaxel formulation with the Taxotere formulation, rats were dosed with either Tween 80 docetaxel (same formulation as Taxotere) or Nab-docetaxel at 5.0, 10.0, 15.0, 30.0, and 50 mg/kg using a 10 minute infusion through indwelling jugular catheters on days 0, 4, and 8 for a total of three treatments. Saline (1 ml/kg/min) was used as a control.

Each animal was observed and weighed daily during days 0-25. Body weight was recorded daily for each treated animal. Signs of clinical distress were recorded daily. Blood was collected on days 13, 16, and day 25 into EDTA-treated tubes and subjected to differential analysis. Necropsy was conducted on day 25.

The result of the study is shown in Table 4. As shown in the table, animals in all dose groups tolerated the first treatment with no acute or infusion related toxicities even at the highest dose of 50 mg/kg. However, only the animals in the lowest dose level of 5 mg/kg and the control saline survived until the end of the experiment (all three treatments). All animals receiving higher doses, died either between the second and third doses or following the third dose.

TABLE 4

Weight loss and Mortality in dose escalation study

| Groups | Maximum % wt. loss | Mortality Observations |
|---|---|---|
| Tween 80-docetaxel | | |
| 50 mg/kg | N/A | 3/3 dead between 2nd and 3rd dose |
| 30 mg/kg | N/A | 3/3 dead between 2nd and 3rd dose |
| 15 mg/kg | N/A | 3/3 dead between 2nd and 3rd dose |
| 10 mg/kg | N/A | 2/3 dead between 2nd and 3rd dose; 1/3 after 3rd dose |
| 5 mg/kg | 24% | 0/3 dead |
| Nab-docetaxel | | |
| 50 mg/kg | N/A | 3/3 dead between 2nd and 3rd dose |
| 30 mg/kg | N/A | 3/3 dead between 2nd and 3rd dose |
| 15 mg/kg | N/A | 3/3 dead between 2nd and 3rd dose |
| 10 mg/kg | N/A | 2/3 dead between 2nd and 3rd dose, 1/3 after 3rd dose |
| 5 mg/kg | 15% | 0/3 dead |
| Control Saline | 3% | 0/3 dead |

Figure 2:
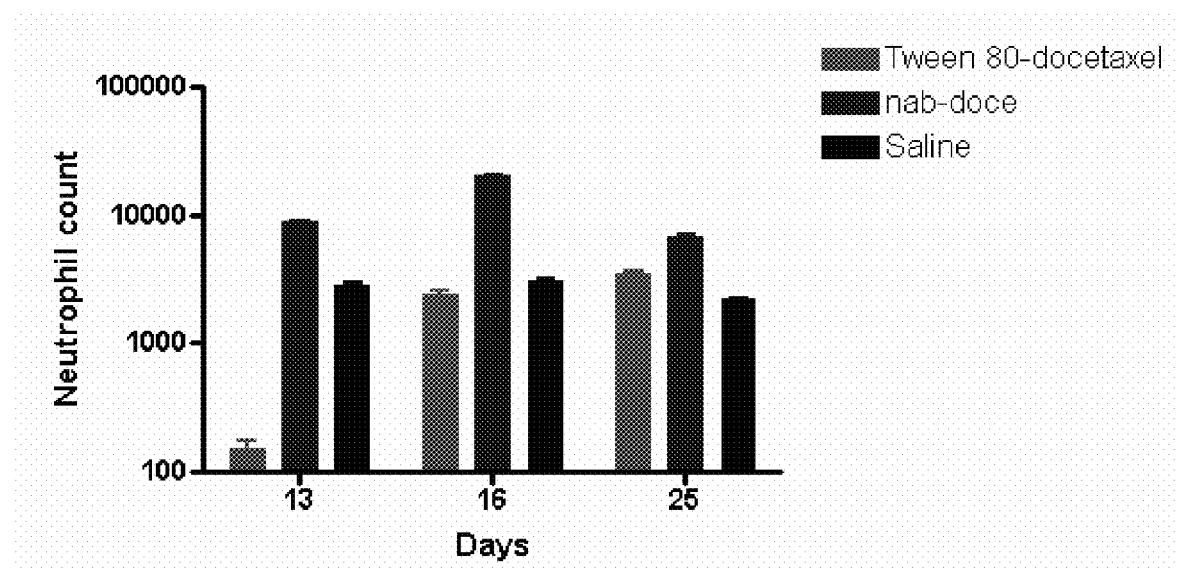
FIG. 2 shows neutropenia comparison in rats at 5 mg/kg dose for Nab-docetaxel and Tween 80-docetaxel (Taxotere®). Dosing occurred on days 0, 4, and 8.

Weight loss of the treated animals is shown in FIG. 1. Neutropenia comparison at 5 mg/kg docetaxel dose for Nab-docetaxel and Tween 80-docetaxel is shown in FIG. 2. Weight loss for the Nab-docetaxel 5 mg/kg surviving group was significantly less than that of the 5 mg/kg Tween-docetaxel group ($p=0.02+$, ANOVA). This was parallel by significantly higher severe neuropenia for Tween-docetaxel (5 mg/kg) versus Nab-docetaxel (5 mg/kg), $p<0.0001$, ANOVA, FIG. 2) on day 13. Necropsy at the end of the experiment (day 25) in the surviving 5 mg/kg groups revealed abnormalities in 2/3 animals in the Tween-docetaxel group (one case of milky fluid accumulation in the thoracic cavity and one case of abnormal spleen adhering to the abdominal wall, stomach, and pancreas). Nab-docetaxel (5 mg/kg) and saline animals were normal.

This pilot study showed significant improvement in safety for Nab-docetaxel in terms of overall body weight loss. Neutropenia was significantly higher for Tween-docetaxel.

Example 34

This example demonstrates the blood kinetics of Nab-docetaxel. All Nab-docetaxel formulations described herein contain 200 mM citrate and 300 mM NaCl.

Rats were divided into six groups (3 per group). On day 1, each animal was weighed and administered a single intravenous dose of the appropriate article show below:

Group A: Taxotere, 10 mg/kg
Group B: Taxotere, 20 mg/kg
Group C: Taxotere, 30 mg/kg
Group D: Nab-docetaxel, 10 mg/kg
Group E: Nab-docetaxel, 20 mg/kg
Group F: Nab-docetaxel, 30 mg/kg The test articles were administered over a 10+/−1 minute infusion period. Blood samples (200 µL) were collected from the tail vein of each rat at the following intervals: Prior to infusion (baseline); during infusion (5 minutes into infusion, $t=-5$ minutes); and at completion of infusion ($t=0$). Blood was also collected at the following time points after completion of infusion: 5, 10, and 20 minutes; 40±3 minutes; 2 hours±5 minutes; 3 hours±10 minutes; 4 hours±10 minutes; 8 hours±10 minutes; 24±1 hours; 48±1 hours; and 120±2 hours. Blood samples were collected in green top (sodium heparin) tubes and processed for collection of plasma by centrifuging at approximately 2,000 rpm for approximately 10 minutes. Plasma samples were stored frozen until shipped on dry ice to ALTA Analytical (El Dorado Hills, Calif.) for LC/MS analysis of docetaxel levels.

Figure 3:
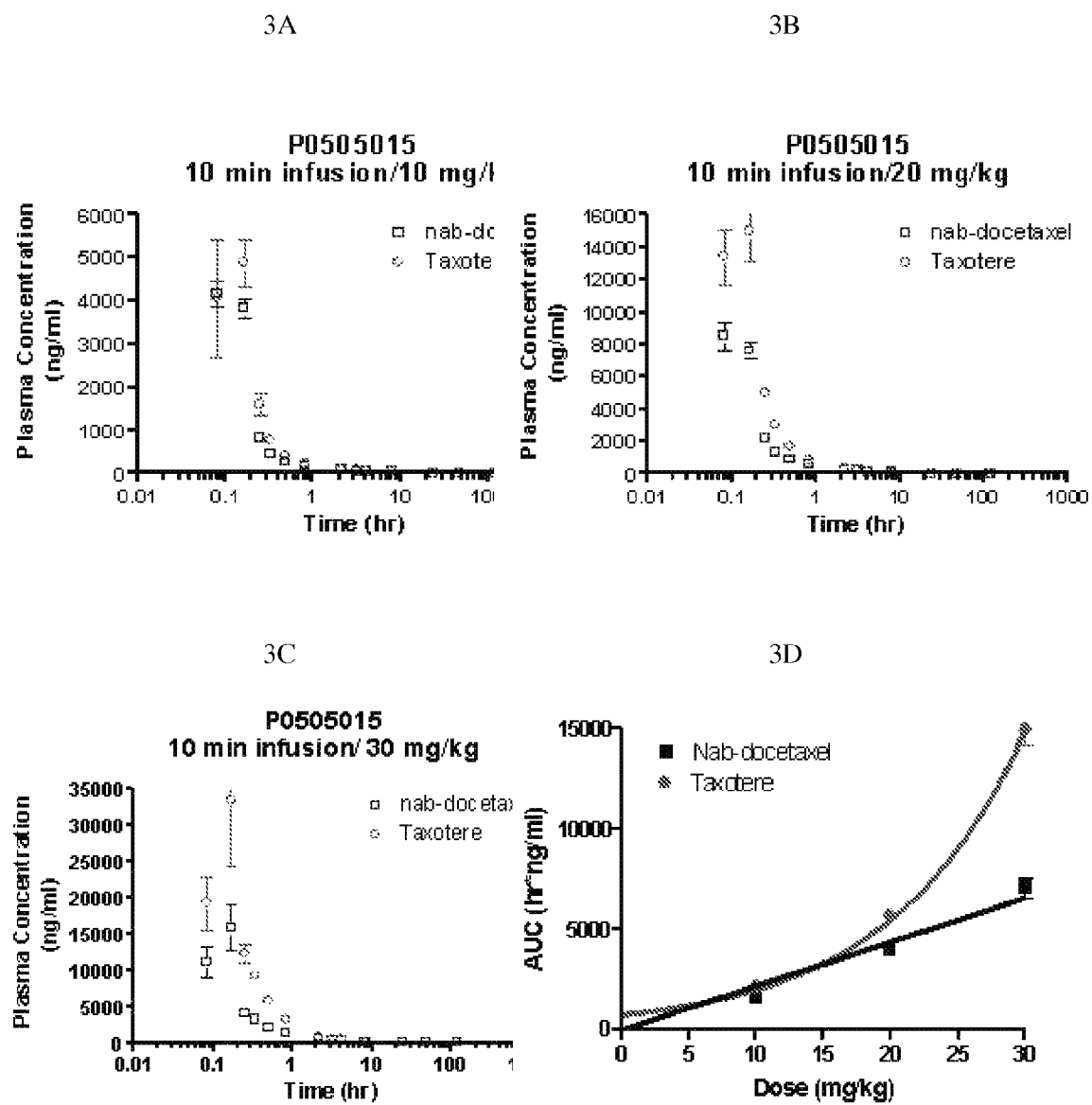
FIGS. 3A-3D show the pharmacokinetic comparison of Nab-docetaxel and Taxotere.

The results of the experiments are shown in FIG. 3 and Table 5. There were no significant differences between the PK profiles of Nab-docetaxel versus Taxotere at 10 mg/kg. However, the differences between Nab-docetaxel and Taxotere were significant at 20 mg/kg with Cmax and AUC, 53% and 70% of Taxotere respectively and Vz and Vss were 177% and 243% of Taxotere respectively. At 30 mg/kg, once again the differences were significant with Cmax and AUC for Nab-docetaxel 46% and 47% of Taxotere respectively and Vz and Vss were 225% and 375% of Taxotere respectively.

TABLE 5

PK Parameters for Nab-docetaxel and Taxotere

| PK Parameters | Nab-docetaxel | Taxotere | p-value |
|---|---|---|---|
| DOSE: 10 mg/kg | | | |
| HL (hr) | 8.3 + 0.3 | 9.0 + 3.2 | ns |
| Tmax (hr) | 0.11 + 0.05 | 0.14 + 0.05 | ns |
| Cmax (ng/ml) | 4,330 + 358 | 4953 + 1,014 | ns |
| AUC inf (hr*ng/ml) | 1,588 + 77 | 2,069 + 615 | ns |
| Vz (L/kg) | 76 + 6 | 63 + 14 | ns |
| Cl (L/hr/kg) | 6.3 + 0.3 | 5.1 + 1.5 | ns |
| Vss (L/kg) | 28 + 1 | 26 + 9 | ns |
| DOSE: 20 mg/kg | | | |
| HL (hr) | 6.3 + 1.8 | 5.1 + 0.31 | ns |
| Tmax (hr) | 0.11 + 0.05 | 0.14 + 0.05 | ns |
| Cmax (ng/ml) | 8,546 + 1,545 | 16,167 + 2,804 | 0.01 |
| AUC inf (hr*ng/ml) | 3,953 + 419 | 5,664 + 500 | 0.01 |
| Vz (L/kg) | 46 + 10 | 26 + 1 | 0.02 |
| Cl (L/hr/kg) | 5.1 + 0.5 | 3.5 + 0.3 | 0.01 |
| Vss (L/kg) | 17 + 4 | 7 + 1 | 0.01 |
| DOSE: 30 mg/kg | | | |
| HL (hr) | 7.3 + 1.0 | 6.9 + 2.9 | ns |
| Tmax (hr) | 0.17 + 0.00 | 0.14 + 0.05 | ns |
| Cmax (ng/ml) | 15,800 + 5,408 | 34,467 + 14,221 | 0.1 |
| AUC inf (hr*ng/ml) | 7,049 + 896 | 14,881 + 1,169 | 0.0008 |
| Vz (L/kg) | 45 + 10 | 20 + 8 | 0.03 |
| Cl (L/hr/kg) | 4.3 + 0.5 | 2.0 + 0.2 | 0.002 |
| Vss (L/kg) | 15 + 4 | 4 + 1 | 0.01 |

When AUC was plotted versus dose, the nonlinearity for Taxotere was clearly evident, with Nab-docetaxel AUC being linear with respect to dose (FIG. 3D). This can be explained by the micelle forming property of Tween 80, the high solubility of docetaxel in the hydrophobic micelle core and corresponding sequestration of docetaxel in the plasma (6). Furthermore, the rapid tissue distribution for Nab-docetaxel may also be explained by utilization of the albumin/caveolae mediated transcytosis via endothelial cells, a process previously described for Abraxane (Nab-paclitaxel).

The PK data suggests that Tween 80 in Taxotere exhibited sequestration of docetaxel in plasma similar to that seen with Cremophor EL in the case of Taxol. This resulted in higher Cmax and AUC and lower volumes of distribution for Taxotere than for Nab-docetaxel. The PK of Nab-docetaxel is linear while that for Tween 80-docetaxel (Taxotere) is non-linear with respect to dose. The dosages described herein, i.e., 10 mg/kg, 20 mg/kg, and 30 mg/kg, are equivalent to a human dosage of about 60 mg/m$^2$, about 120 mg/m$^2$, and about 180 mg/m$^2$. Typically, the linear range of PK of the Nab-docetaxel is about 10-180 mg/m$^2$.

Example 35

This example demonstrates the inhibition of drug-albumin interaction by surfactants such as Tween 80. The experiment was done using a fluorescent-labelled paclitaxel (Flutax) as a surrogate for paclitaxel/docetaxel. Flutax was shown to have similar binding to albumin as paclitaxel.

HSA was immobilized on 96 well plastic microplate. The immobilized albumin was reacted for 1 hr with constant concentration of Flutax and increasing concentration of solvents (Cremophor EL/EtOH, Tween 80, and TPGS). The unbound ligands were washed off with buffer. Bound ligands were quantitated using a fluorometer. The IC50 was determined using an exponential decay equation.

Figure 4:
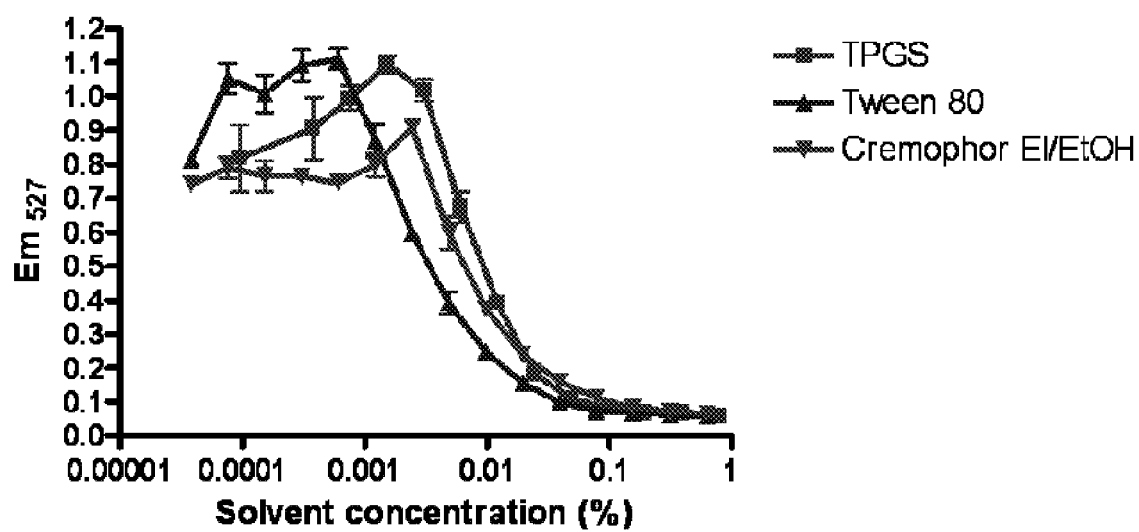
FIG. 4 shows the inhibition of drug binding to albumin in the presence of surfactant Tween 80 and Cremophor EL®/EtOH.

The results of the experiment were shown in FIG. 4. As shown in FIG. 4, albumin-paclitaxel interaction was inhibited by solvent commonly used in the formulation of water insoluble drug such as Cremophor EL/EtOH, Tween 80, and TPGS (IC50 of 0.009%, 0.003%, and 0.008%, respectively). Complete inhibition occurred at 0.02% or 0.2 µl Tween 80/ml. This is clinically relevant as Taxotere treated patients exhibited 0.07-0.41 µl of Tween 80/ml of blood at the end of drug infusion.

This experiment demonstrates that Tween 80 in the Taxotere formulation may inhibit binding of docetaxel to albumin and prevent its endothelial transcytosis via the gp60/caveolar mechanism. The PK data in the above studies also support this observation.

Example 36

This example provides evaluation of antitumor activity of Nab-docetaxel against H29 colon carcinoma xenograft in athymic nude mice. The mice were divided into the control group and the Nab-docetaxel group (N=4 mice per group, each with bilateral tumors). All Nab-docetaxel formulations described herein contain 200 mM citrate and 300 mM NaCl.

Briefly, H29 tumors were implanted subcutaneously in athymic nude mice, allowed to grow to 100 mm$^3$ and then treated with either the control (no drug) or Nab-docetaxel (15 mg/kg, q4dx3, iv bolus). Tumor size and body weight measurements were obtained three times weekly and plotted in FIG. 5.

Figure 5:
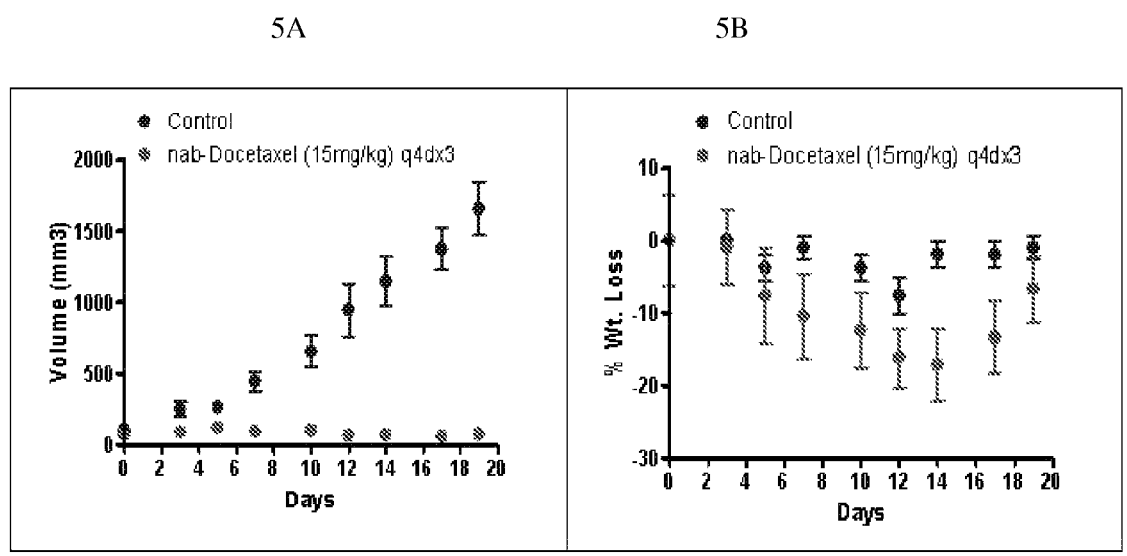
FIGS. 5A and 5B show antitumor activity (5A) and body weight loss (5B) with Nab-docetaxel in a H29 colon tumor xenograft mice. Mice were dosed with Nab-docetaxel at 15 mg/kg, q4dx3.

As shown in FIG. 5, there was significant inhibition of HT29 tumor in vivo, p<0.0001 vs control, ANOVA. At the 15 mg/kg dose of Nab-docetaxel, mean weight loss between 10-20% suggesting that this dose may be close to the MTD for Nab-docetaxel. The MTD for Taxotere has been reported to be 15 mg/kg on this schedule.

Example 37

This example compares the antitumor activity of Nab-docetaxel and Taxotere using the HCT116 colon carcinoma xenograft in athymic nude mice with a 50% higher dose of Nab-docetaxel as compared to Taxotere. The mice were divided into the control group, the Nab-docetaxel group, and the Taxotere group (N=10 mice per group). All Nab-docetaxel formulations described herein contain 200 mM citrate and 300 mM NaCl.

Briefly, antitumor activity of Nab-docetaxel and Taxotere were compared at doses of 22 mg/kg q4×3 and 15 mg/kg q4×3, respectively in the HCT116 colon carcinoma xenograft. The results of the experiments are shown in FIG. 6.

Figure 6:
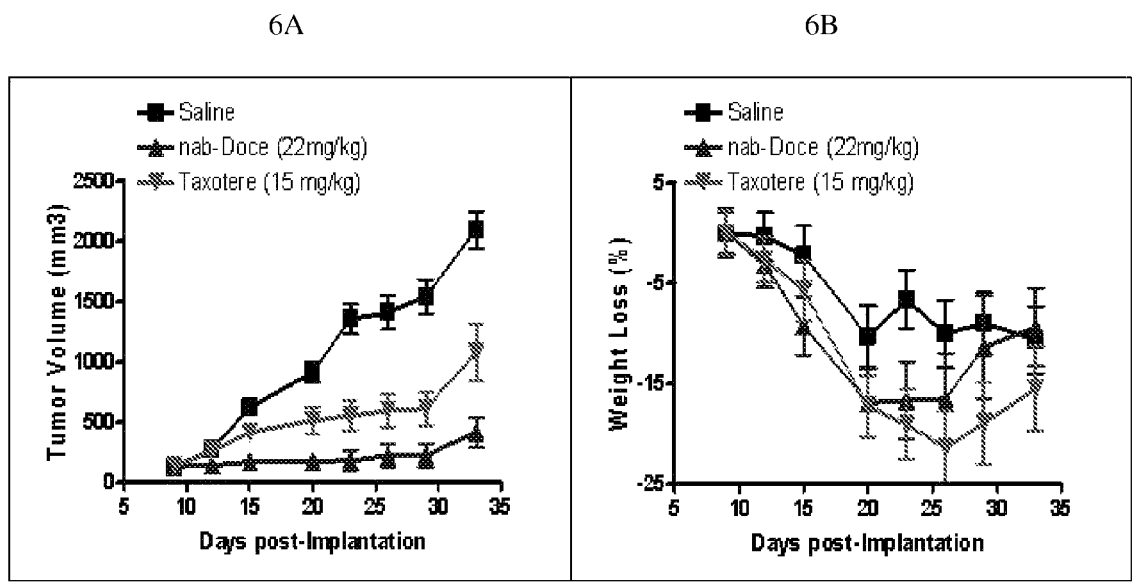
FIGS. 6A and 6B show antitumor activity (6A) and body weight loss (6B) in a HCT116 colon tumor xenograft mouse dosed with saline, Nab-docetaxel (22 mg/kg), and Taxotere (15 mg/kg).

As shown in FIG. 6, both Nab-docetaxel and Taxotere showed tumor inhibition with respect to the control. As shown below tumor inhibition was improved with Nab-docetaxel versus Taxotere (p=0.03, ANOVA) and weight loss was somewhat lower but not statistically significant (p=ns, ANOVA) between the two groups.

In this pilot study, the antitumor activity of Nab-docetaxel was superior to that of Taxotere. The mice tolerated 50% higher docetaxel dose for Nab-docetaxel with somewhat lower overall body weight loss compared to Taxotere.

Example 38

This example compares the toxicity of Nab-docetaxel preparation with stabilizers (citrate/NaCl) vs Taxotere (Tween-docetaxel) in rats given a single dose of each preparation.

Male Sprague-Dawley rats (160-180 g, n=3/group) were infused with Taxotere, or Nab-docetaxel (citrate/NaCl) Infusion time was 10 minutes and the following dose levels of docetaxel were used: 25, 50, 75, 100, and 125 mg/kg. The animals were weighed and monitored daily for signs of toxicity/mortality. Percent mortality (%) at 7 days following treatment were shown in Table 6.

TABLE 6

Percent mortality in rats treated by Taxotere and Nab-docetaxel.

| | Dose (mg/kg) | | | | |
| --- | --- | --- | --- | --- | --- |
| | 125 | 100 | 75 | 50 | 25 |
| Taxotere | 100% | 100% | 100% | 100% | 100% |
| Nab-docetaxel (+citrate) | 66% | 66% | 100% | 33% | 0% |

As shown in Table 6, the Nab-docetaxel formulation were significantly less toxic than Taxotere (Tween-docetaxel). This effect was particularly pronounced at doses of 25 and 50 mg/kg. The LD50 was calculated to be 63 mg/kg for Nab-docetaxel versus approximately 12.5 mg/kg for Tween-docetaxel.

Example 39

This example shows the efficacy of Nab-docetaxel in treatment of prostate cancer in a PC3 prostate xenograft tumor model.

PC3 tumor were implanted subcutaneously in athymic nude mice, allowed to grow to 100 mm$^3$ and then treated q4×3, i.v. with either the saline or Nab-docetaxel (10, 15, 20, or 30 mg/kg) or Tween-docetaxel (10 mg/kg). Six mice in each group were evaluated.

Figure 7:
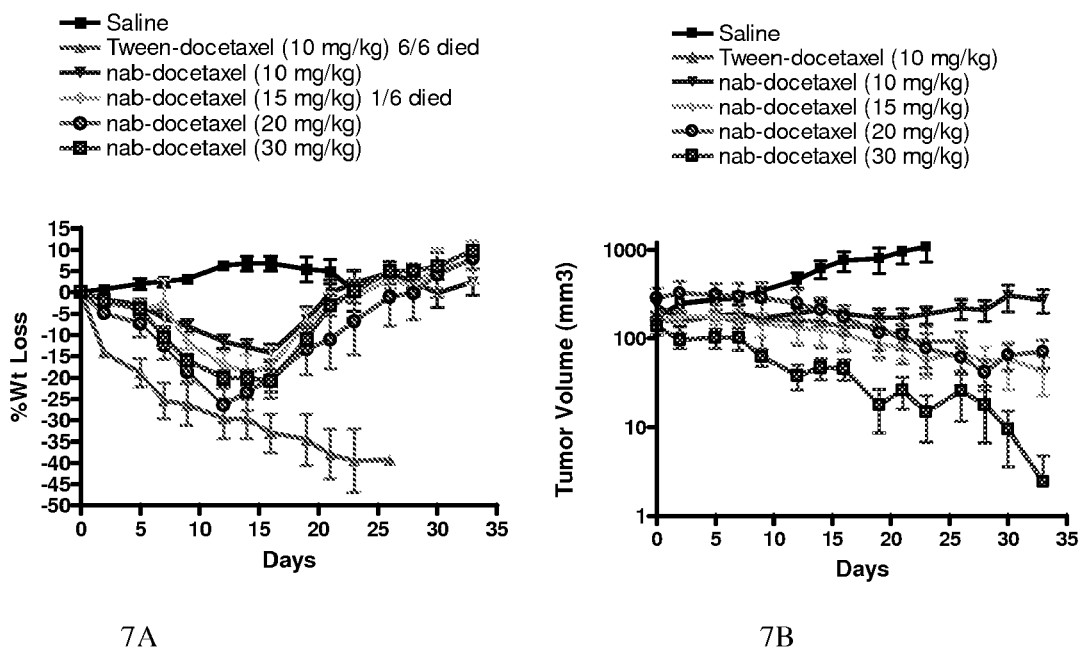
FIGS. 7A and 7B show body weight loss (7A) and antitumor activity (7B) in a PC3 prostate tumor xenograft mouse dosed with saline, Nab-docetaxel (10, 15, 20, 30 mg/kg), and Tween 80-docetaxel (10 mg/kg).

The results of the study are shown in FIG. 7. All six Tween-docetaxel treated mice died over the course of the study. By contrast, Nab-docetaxel was well tolerated at all dose levels. There was only one death at 15 mg/kg, and none was observed at the higher dose levels of 20 mg/kg and 30 mg/kg. Tumor suppression was observed at all dose levels of Nab-docetaxel. In particular, at 30 mg/kg dose, there were six out of six complete regressions.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

The invention claimed is:

1. A composition comprising 1) nanoparticles comprising docetaxel coated with a carrier protein, wherein said carrier protein is albumin and 2) a citrate selected from the group consisting of citric acid and sodium citrate, wherein stability of the composition is enhanced as compared to that of a composition without citric acid or sodium citrate.

2. The composition according to claim 1, wherein the ratio of albumin to docetaxel is about 18:1 or less.

3. The composition according to claim 1, wherein the nanoparticles in the composition have an average or mean particle size of no greater than about 200 nm.

4. The composition according to claim 1, wherein the composition is a liquid suspension of docetaxel at a concentration of at least about 1 mg/ml.

5. The composition according to claim 1, wherein the composition is a dry composition that can be reconstituted to a liquid suspension with at least about 1 mg/ml docetaxel.

6. The composition according to claim 1, wherein the composition further comprises sodium chloride.

7. The composition according to claim 6, wherein the composition comprises about 200 mM sodium citrate and about 300 mM sodium chloride.

8. The composition according to claim 1, wherein the albumin is human serum albumin.

9. The composition according to claim 1, wherein the citrate is sodium citrate.

10. The composition according to claim 1, wherein the pH of the composition is no less than about 6.

11. The composition according to claim 1, wherein the composition is stable for at least about 24 hours following reconstitution or rehydration.

12. The composition according to claim 8, wherein the composition further comprises sodium chloride.

13. The composition according to claim 8, wherein the citrate is sodium citrate.

14. The composition according to claim 13, further comprising sodium chloride.

* * * * *